United States Patent
Minassian et al.

(10) Patent No.: US 11,946,065 B2
(45) Date of Patent: Apr. 2, 2024

(54) TRANSGENE CASSETTES, AAV VECTORS, AND AAV VIRAL VECTORS FOR EXPRESSION OF HUMAN CODON-OPTIMIZED CSTB

(71) Applicant: THE BOARD OF REGENTS OF THE UNIVERSITY OF TEXAS SYSTEM, Austin, TX (US)

(72) Inventors: Berge A. Minassian, Dallas, TX (US); Emrah Gumusgoz, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/387,035

(22) Filed: Jul. 28, 2021

(65) Prior Publication Data
US 2022/0049270 A1 Feb. 17, 2022

Related U.S. Application Data

(60) Provisional application No. 63/058,038, filed on Jul. 29, 2020.

(51) Int. Cl.
| | |
|---|---|
| C12N 15/864 | (2006.01) |
| C12N 7/00 | (2006.01) |
| C12N 15/11 | (2006.01) |
| C12N 15/113 | (2010.01) |
| C12N 15/15 | (2006.01) |
| C12N 15/86 | (2006.01) |

(52) U.S. Cl.
CPC ............. *C12N 15/86* (2013.01); *C12N 7/00* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 2011/0014602 A1 | 1/2011 | Kim et al. | |
| 2012/0077860 A1 | 3/2012 | Garcia | |
| 2014/0010861 A1 | 1/2014 | Bancel et al. | |
| 2014/0310830 A1 | 10/2014 | Zhang et al. | |
| 2017/0020994 A1 | 1/2017 | Bloom et al. | |
| 2017/0128528 A1 | 5/2017 | Samulski | |
| 2019/0076550 A1 | 3/2019 | Wang et al. | |
| 2019/0241633 A1 | 8/2019 | Shoji | |
| 2020/0148745 A1 | 5/2020 | Keravala et al. | |
| 2021/0139934 A1* | 5/2021 | Gray | C07K 14/70571 |
| 2021/0330811 A1* | 10/2021 | Gray | A61P 25/28 |
| 2021/0330814 A1* | 10/2021 | Simons | C07K 14/47 |

FOREIGN PATENT DOCUMENTS

| | | |
|---|---|---|
| WO | 2017191274 A2 | 11/2017 |

OTHER PUBLICATIONS

Maher et al, A Role for Stefin B (Cystatin B) in Inflammation and Endotoxemia, JBC, 2014, pp. 31736-31750.*
Riva et al, Emerging treatments for progressive myoclonus epilepsies, Expert Rev Neurother. Apr. 2020 ; 20(4): 341-350.*
Inouye et al, Codon optimization of genes for efficient protein expression in mammalian cells by selection of only preferred human codons, Protein Expression and Purification 109 (2015) 47-54.*
Wang et al, Adeno-associated virus vector as a platform for gene therapy delivery, Nature, 2019, pp. 358-378.*
Zimmern et al, A Review of Targeted Therapies for Monogenic Epilepsy Syndromes, Frontiers in Neurology, 2022, pp. 1-13.*
Matos et al, Correction of a Splicing Mutation Affecting an Unverricht-Lundborg Disease Patient by Antisense Therapy, Genes, 2018, pp. 1-9.*
Hudry and Vandenberghe, Therapeutic AAV Gene Transfer to the Nervous System: A Clinical Reality, Neuron, 2019, pp. 839-862, plus correction page Neuron, 2019, p. 239.*
PCT International Application No. PCT/US2021/043401 International Search Report of The International Searching Authority, dated Nov. 22, 2021, 5 pages.
PCT International Application No. PCT/US2021/043401 Written Opinion of The International Searching Authority, dated Nov. 22, 2021, 10 pages.

* cited by examiner

*Primary Examiner* — Maria Marvich
(74) *Attorney, Agent, or Firm* — DLA Piper LLP US

(57) ABSTRACT

The present disclosure provides methods and compositions for the treatment of diseases and genetic disorders linked to CSTB loss and/or misfunction. The methods and compositions of the present disclosure include rAAV vectors and rAAV viral vectors comprising transgene nucleic acid molecules encoding CSTB polypeptides.

13 Claims, 13 Drawing Sheets
Specification includes a Sequence Listing.

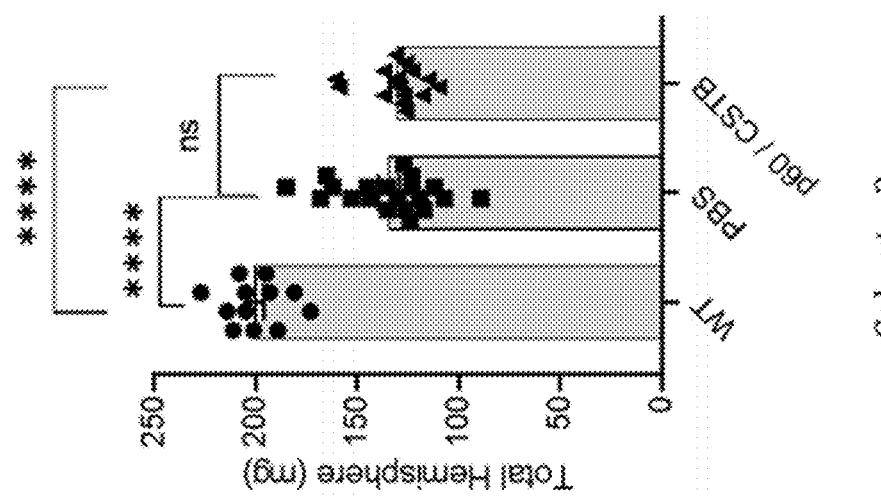
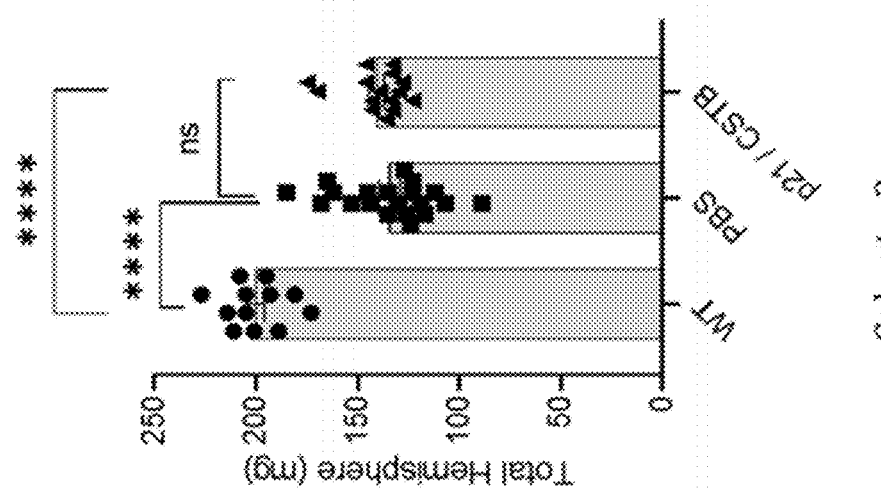
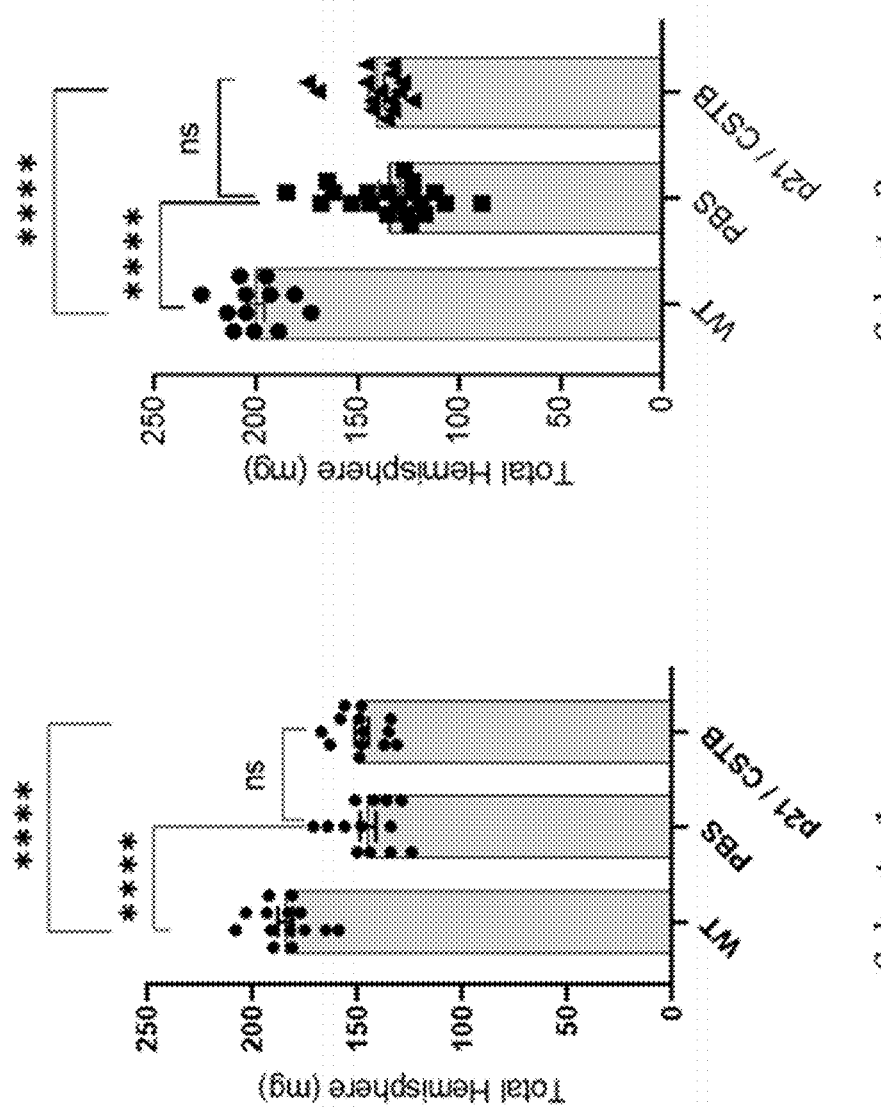

SEQUENCE LISTING

```
<160> NUMBER OF SEQ ID NOS: 15

<210> SEQ ID NO 1
<211> LENGTH: 5245
<212> TYPE: DNA
<213> ORGANISM: Artificial Sequence
<220> FEATURE:
<223> OTHER INFORMATION: Nucleic acid molecule pscAAV CBh hCSTB

<400> SEQUENCE: 1
tgcgcgctcg ctcgctcact gaggccgccc gggcaaagcc cgggcgtcgg gcgacctttg      60
gtcgcccggc ctcagtgagc gagcgagcgc gcagagaggg agtgggggttc ggtacccgtt     120 acataactta cggtaaatgg cccgcctggc tgaccgccca acgaccccccg cccattgacg     180 tcaataatga cgtatgttcc catagtaacg ccaatagggga ctttccattg acgtcaatgg     240
gtggagtatt tacggtaaac tgcccacttg gcagtacatc aagtgtatca tatgccaagt     300 acgccccta ttgacgtcaa tgacggtaaa tggcccgcct ggcattatgc ccagtacatg      360
accttatggg actttcctac ttggcagtac atctacgtat tagtcatcgc tattaccatg     420
```

-continued

```
gtcgaggtga gccccacgtt ctgcttcact ctccccatct cccccccctc cccaccccca    480
attttgtatt tatttattt ttaattattt tgtgcagcga tggggcggg ggggggggg      540 gggcgcgcgc caggcggggc ggggcggggc gaggggcggg gcggggcgag gcggagaggt   600
gcggcggcag ccaatcagag cggcgcgctc cgaaagtttc cttttatggc gaggcggcgg   660
cggcggcggc cctataaaaa gcgaagcgcg cggcgggcgg gagtcgctgc gacgctgcct   720
tcgccccgtg ccccgctccg ccgccgcctc gcgccgcccg ccccggctct gactgaccgc   780
gttactccca caggtgagcg ggcgggacgg cccttctcct ccgggctgta attagctgag   840
caagaggtaa gggtttaagg gatggttggt tggtggggta ttaatgttta attacctgga   900
gcacctgcct gaaatcactt ttttcaggt tggaaccggt gccaccatga tgtgcggagc    960
cccttcagcc acccaacccg ccactgccga gacacagcat attgccgacc aagtccggtc   1020
gcagttggaa gaaaaggaaa acaagaaatt cccggtgttc aaggcagtgt ccttcaagtc   1080
ccaagtcgtg gcggggacta attacttcat caaagtgcac gtcggcgatg aggacttcgt   1140
gcatctgcgc gtgtttcagt cccttccgca cgagaacaag ccactcaccc tgagcaacta   1200
ccagaccaac aaggctaagc acgacgaact gacctacttc taagcggccg cgcgcggatc   1260
cctcgactgt gccttctagt tgccagccat ctgttgtttg cccctccccc gtgccttcct   1320
tgaccctgga aggtgccact cccactgtcc tttcctaata aaatgaggaa attgcatcgc   1380
attgtctgag taggtgtcat tctattctgg ggggtggggt ggggcaggac agcaagggg    1440 aggattggga agacaacagc aggcatgctg gggatgcggt gggctctatg gcttctgagg   1500
cggaaagaac cagctacgcg taggaacccc tagtgatgga gttggccact ccctctctgc   1560
gcgctcgctc gctcactgag gccgggcgac caaaggtcgc ccgacgcccg ggctttgccc   1620
gggcggcctc agtgagcgag cgagcgcgcc agctggcgta atagcgaaga ggcccgcacc   1680
gatcgccctt cccaacagtt gcgcagcctg aatggcgaat ggaattccag acgattgagc   1740
gtcaaaatgt aggtatttcc atgagcgttt ttcctgttgc aatggctggc ggtaatattg   1800
ttctggatat taccagcaag gccgatagtt tgagttcttc tactcaggca agtgatgtta   1860
ttactaatca agaagtatt gcgacaacgg ttaatttgcg tgatggacag actcttttac    1920
tcggtggcct cactgattat aaaaacactt ctcaggattc tggcgtaccg ttcctgtcta   1980 aaatccctt aatcggcctc ctgtttagct cccgctctga ttctaacgag gaaagcacgt    2040
tatacgtgct cgtcaaagca accatagtac gcgccctgta gcggcgcatt aagcgcggcg   2100
ggtgtggtgg ttacgcgcag cgtgaccgct acacttgcca gcgccctagc gcccgctcct   2160
ttcgctttct tcccttcctt tctcgccacg ttcgccggct ttccccgtca gctctaaat    2220 cgggggctcc ctttagggtt ccgatttagt gctttacggc acctcgaccc caaaaaactt   2280
gattagggtg atggttcacg tagtgggcca tcgccctgat agacggtttt tcgccctttg   2340
acgttggagt ccacgttctt taatagtgga ctcttgttcc aaactggaac aacactcaac   2400
cctatctcgg tctattcttt tgatttataa gggattttgc cgatttcggc ctattggtta   2460
aaaaatgagc tgatttaaca aaaatttaac gcgaatttta acaaaatatt aacgcttaca   2520
atttaaatat ttgcttatac aatcttcctg ttttggggc ttttctgatt atcaaccggg    2580
gtacatatga ttgacatgct agttttacga ttaccgttca tcgattctct tgtttgctcc   2640
agactctcag gcaatgacct gatagccttt gtagagacct ctcaaaaata gctaccctct   2700
ccggcatgaa tttatcagct agaacggttg aatatcatat tgatggtgat ttgactgtct   2760
ccggcctttc tcacccgttt gaatctttac ctacacatta ctcaggcatt gcatttaaaa   2820
```

```
tatatgaggg ttctaaaaat ttttatcctt gcgttgaaat aaaggcttct cccgcaaaag   2880
tattacaggg tcataatgtt tttggtacaa ccgatttagc tttatgctct gaggctttat   2940
tgcttaattt tgctaattct ttgccttgcc tgtatgattt attggatgtt ggaatcgcct   3000
gatgcggtat tttctcctta cgcatctgtg cggtatttca caccgcatat ggtgcactct   3060
cagtacaatc tgctctgatg ccgcatagtt aagccagccc cgacaccgc caacacccgc    3120 tgacgcgccc tgacgggctt gtctgctccc ggcatccgct tacagacaag ctgtgaccgt   3180
ctccgggagc tgcatgtgtc agaggttttc accgtcatca ccgaaacgcg cgagacgaaa   3240
gggcctcgtg atacgcctat ttttataggt taatgtcatg ataataatgg tttcttagac   3300
gtcaggtggc acttttcggg gaatgtgcg cggaaccct atttgtttat ttttctaaat     3360
acattcaaat atgtatccgc tcatgagaca ataaccctga taaatgcttc aataatattg   3420
aaaaaggaag agtatgagcc atattcaacg ggaaacgtct tgctctaggc gcgattaaa    3480 ttccaacatg gatgctgatt tatatgggta taaatgggct cgcgataatg tcgggcaatc   3540
aggtgcgaca atctatcgat tgtatgggaa gcccgatgcg ccagagttgt ttctgaaaca   3600
tggcaaaggt agcgttgcca atgatgttac agatgagatg gtcagactaa actggctgac   3660
ggaatttatg cctcttccga ccatcaagca ttttatccgt actcctgatg atgcatggtt   3720
actcaccact gcgatccctg ggaaaacagc attccaggta ttagaagaat atcctgattc   3780
aggtgaaaat attgttgatg cgctggcagt gttcctgcgc cggttgcatt cgattcctgt   3840
ttgtaattgt cctttttaaca gcgatcgcgt atttcgtctc gctcaggcgc aatcacgaat   3900
gaataacggt ttggttgatg cgagtgattt tgatgacgag cgtaatggct ggcctgttga   3960
acaagtctgg aaagaaatgc ataaacttttt gccattctca ccggattcag tcgtcactca   4020
tggtgatttc tcacttgata accttatttt tgacgagggg aaattaatag gttgtattga   4080
tgttggacga gtcggaatcg cagaccgata ccaggatctt gccatcctat ggaactgcct   4140
cggtgagttt tctccttcat tacagaaacg gcttttttcaa aaatatggta ttgataatcc   4200
tgatatgaat aaaattgcagt ttcatttgat gctcgatgag ttttttctaac tgtcagacca   4260 agtttactca tatatacttt agattgattt aaaacttcat ttttaattta aaaggatcta   4320
ggtgaagatc cttttttgata atctcatgac caaaatccct taacgtgagt tttcgttcca   4380
ctgagcgtca gaccccgtag aaaagatcaa aggatcttct tgagatcctt tttttctgcg   4440
cgtaatctgc tgcttgcaaa caaaaaaacc accgctacca gcggtggttt gtttgccgga   4500
tcaagagcta ccaactcttt ttccgaaggt aactggcttc agcagagcgc agataccaaa   4560
tactgttctt ctagtgtagc cgtagttagg ccaccacttc aagaactctg tagcaccgcc   4620
tacatacctc gctctgctaa tcctgttacc agtggctgct gccagtggcg ataagtcgtg   4680
tcttaccggg ttggactcaa gacgatagtt accggataag gcgcagcggt cgggctgaac   4740
ggggggttcg tgcacacagc ccagcttgga gcgaacgacc tacaccgaac tgagatacct   4800
acagcgtgag ctatgagaaa gcgccacgct tcccgaaggg agaaaggcgg acaggtatcc   4860
ggtaagcggc agggtcggaa caggagagcg cacgagggag cttccagggg gaaacgcctg   4920
gtatctttat agtcctgtcg ggtttcgcca cctctgactt gagcgtcgat ttttgtgatg   4980
ctcgtcaggg gggcggagcc tatggaaaaa cgccagcaac gcggcctttt tacggttcct   5040
ggccttttgc tggccttttg ctcacatgtt ctttcctgcg ttatcccctg attctgtgga   5100
taaccgtatt accgcctttg agtgagctga taccgctcgc cgcagccgaa cgaccgagcg   5160
```

```
cagcgagtca gtgagcgagg aagcggaaga gcgcccaata cgcaaaccgc ctctccccgc    5220
gcgttggccg attcattaat gcagc                                         5245
```

<210> SEQ ID NO 2
<211> LENGTH: 105
<212> TYPE: DNA
<213> ORGANISM: Artificial Sequence
<220> FEATURE:
<223> OTHER INFORMATION: ITR Derived from AAV2-FLIP- Mutated for
      scGenome

<400> SEQUENCE: 2

```
tgcgcgctcg ctcgctcact gaggccgccc gggcaaagcc cgggcgtcgg gcgacctttg    60
gtcgcccggc ctcagtgagc gagcgagcgc gcagagaggg agtgg                   105
```

<210> SEQ ID NO 3
<211> LENGTH: 812
<212> TYPE: DNA
<213> ORGANISM: Artificial Sequence
<220> FEATURE:
<223> OTHER INFORMATION: CBh hybrid promoter

<400> SEQUENCE: 3

```
cgttacataa cttacggtaa atggcccgcc tggctgaccg cccaacgacc cccgcccatt    60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catggtcgag gtgagcccca cgttctgctt cactctcccc atctcccccc cctccccacc    360
cccaattttg tatttattta ttttttaatt attttgtgca gcgatggggg cggggggggg    420
gggggggcgc gcgccaggcg gggcggggcg gggcgagggg cggggcgggg cgaggcggag    480
aggtgcggcg gcagccaatc agagcggcgc gctccgaaag tttccttttt atggcgaggcg    540 gcggcggcgg cggccctata aaaagcgaag cgcgcggcgg gcgggagtcg ctgcgacgct    600
gccttcgccc cgtgccccgc tccgccgccg cctcgcgccg cccgccccgg ctctgactga    660
ccgcgttact cccacaggtg agcgggcggg acggcccttc tcctccgggc tgtaattagc    720
tgagcaagag gtaagggttt aagggatggt tggttggtgg gtattaatgt ttaattacc    780 tggagcacct gcctgaaatc acttttttc ag                                 812
```

<210> SEQ ID NO 4
<211> LENGTH: 304
<212> TYPE: DNA
<213> ORGANISM: Artificial Sequence
<220> FEATURE:
<223> OTHER INFORMATION: CMV enhancer

<400> SEQUENCE: 4

```
cgttacataa cttacggtaa atggcccgcc tggctgaccg cccaacgacc cccgcccatt    60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catg                                                                304
```

<210> SEQ ID NO 5
<211> LENGTH: 278
<212> TYPE: DNA
<213> ORGANISM: Artificial Sequence
<220> FEATURE:
<223> OTHER INFORMATION: CBA Promoter

<400> SEQUENCE: 5

```
tcgaggtgag ccccacgttc tgcttcactc tccccatctc cccccctcc ccaccccaa      60
ttttgtattt atttattttt taattatttt gtgcagcgat ggggggcgggg gggggggggg  120
ggcgcgcgcc aggcggggcg gggcggggcg aggggcgggg cggggcgagg cggagaggtg  180
cggcggcagc caatcagagc ggcgcgctcc gaaagtttcc ttttatggcg aggcggcggc  240
ggcggcggcc ctataaaaag cgaagcgcgc ggcgggcg                          278
```

<210> SEQ ID NO 6
<211> LENGTH: 229
<212> TYPE: DNA
<213> ORGANISM: Artificial Sequence
<220> FEATURE:
<223> OTHER INFORMATION: Hybrid intron

<400> SEQUENCE: 6

```
ggagtcgctg cgacgctgcc ttcgccccgt gccccgctcc gccgccgcct cgcgccgccc    60
gccccggctc tgactgaccg cgttactccc acaggtgagc gggcgggacg gcccttctcc  120
tccgggctgt aattagctga gcaagaggta agggtttaag ggatggttgg ttggtggggt  180
attaatgttt aattacctgg agcacctgcc tgaaatcact ttttttcag              229
```

<210> SEQ ID NO 7
<211> LENGTH: 43
<212> TYPE: DNA
<213> ORGANISM: Artificial Sequence
<220> FEATURE:
<223> OTHER INFORMATION: CBA Intron 1

<400> SEQUENCE: 7

```
gtgagcgggc gggacggccc ttctcctccg ggctgtaatt agc                     43
```

<210> SEQ ID NO 8
<211> LENGTH: 92
<212> TYPE: DNA
<213> ORGANISM: Artificial Sequence
<220> FEATURE:
<223> OTHER INFORMATION: MVM Intron

<400> SEQUENCE: 8

```
aagaggtaag ggtttaaggg atggttggtt ggtggggtat taatgtttaa ttacctggag    60
cacctgcctg aaatcacttt ttttcaggtt gg                                 92
```

<210> SEQ ID NO 9
<211> LENGTH: 317
<212> TYPE: DNA
<213> ORGANISM: Artificial Sequence
<220> FEATURE:
<223> OTHER INFORMATION: hCSTB

<400> SEQUENCE: 9

```
accggtgcca ccatgatgtg cggagcccct tcagccaccc aacccgccac tgccgagaca    60
cagcatattg ccgaccaagt ccggtcgcag ttggaagaaa aggaaaacaa gaaattcccg  120
gtgttcaagg cagtgtcctt caagtcccaa gtcgtggcgg ggactaatta cttcatcaaa  180
```

```
gtgcacgtcg gcgatgagga cttcgtgcat ctgcgcgtgt ttcagtccct tccgcacgag   240
aacaagccac tcaccctgag caactaccag accaacaagg ctaagcacga cgaactgacc   300
tacttctaag cggccgc                                                  317
```

<210> SEQ ID NO 10
<211> LENGTH: 225
<212> TYPE: DNA
<213> ORGANISM: Artificial Sequence
<220> FEATURE:
<223> OTHER INFORMATION: Bovine Growth Hormone polyA

<400> SEQUENCE: 10

```
ctgtgccttc tagttgccag ccatctgttg tttgcccctc ccccgtgcct tccttgaccc    60
tggaaggtgc cactcccact gtcctttcct aataaaatga ggaaattgca tcgcattgtc   120
tgagtaggtg tcattctatt ctggggggtg gggtggggca ggacagcaag ggggaggatt   180
gggaagacaa cagcaggcat gctggggatg cggtgggctc tatgg                   225
```

<210> SEQ ID NO 11
<211> LENGTH: 145
<212> TYPE: DNA
<213> ORGANISM: Artificial Sequence
<220> FEATURE:
<223> OTHER INFORMATION: ITR Derived from AAV2-FLOP

<400> SEQUENCE: 11

```
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcca gctggcgtaa tagcg                                         145
```

<210> SEQ ID NO 12
<211> LENGTH: 514
<212> TYPE: DNA
<213> ORGANISM: Artificial Sequence
<220> FEATURE:
<223> OTHER INFORMATION: M13 bacteriophage origin of replication

<400> SEQUENCE: 12

```
acgcgccctg tagcggcgca ttaagcgcgg cgggtgtggt ggttacgcgc agcgtgaccg    60
ctacacttgc cagcgcccta gcgcccgctc ctttcgcttt cttcccttcc tttctcgcca   120
cgttcgccgg ctttccccgt caagctctaa atcgggggct ccctttaggg ttccgattta   180
gtgctttacg gcacctcgac cccaaaaaac ttgattaggg tgatggttca cgtagtgggc   240
catcgccctg atagacggtt tttcgccctt tgacgttgga gtccacgttc tttaatagtg   300
gactcttgtt ccaaactgga acaacactca accctatctc ggtctattct tttgatttat   360
aagggatttt gccgatttcg gcctattggt taaaaaatga gctgatttaa caaaaattta   420
acgcgaattt taacaaaata ttaacgctta caatttaaat atttgcttat acaatcttcc   480
tgttttgggg ctttttctga ttatcaaccg gggt                              514
```

<210> SEQ ID NO 13
<211> LENGTH: 105
<212> TYPE: DNA
<213> ORGANISM: Artificial Sequence
<220> FEATURE:
<223> OTHER INFORMATION: AmpR promoter

<400> SEQUENCE: 13

```
cgcggaaccc ctatttgttt attttttctaa atacattcaa atatgtatcc gctcatgaga    60
caataaccct gataaatgct tcaataatat tgaaaaagga agagt                    105
```

<210> SEQ ID NO 14
<211> LENGTH: 816
<212> TYPE: DNA
<213> ORGANISM: Artificial Sequence
<220> FEATURE:
<223> OTHER INFORMATION: KanR

<400> SEQUENCE: 14

```
atgagccata ttcaacggga aacgtcttgc tctaggccgc gattaaattc caacatggat     60
gctgatttat atgggtataa atgggctcgc gataatgtcg ggcaatcagg tgcgacaatc    120
tatcgattgt atgggaagcc cgatgcgcca gagttgtttc tgaaacatgg caaaggtagc    180
gttgccaatg atgttacaga tgagatggtc agactaaact ggctgacgga atttatgcct    240
cttccgacca tcaagcattt tatccgtact cctgatgatg catggttact caccactgcg    300
atccctggga aaacagcatt ccaggtatta gaagaatatc ctgattcagg tgaaaatatt    360
gttgatgcgc tggcagtgtt cctgcgccgg ttgcattcga ttcctgtttg taattgtcct    420
tttaacagcg atcgcgtatt tcgtctcgct caggcgcaat cacgaatgaa taacggtttg    480
gttgatgcga gtgattttga tgacgagcgt aatggctggc ctgttgaaca agtctggaaa    540
gaaatgcata acttttgcc attctcaccg gattcagtcg tcactcatgg tgatttctca    600
cttgataacc ttatttttga cgaggggaaa ttaataggtt gtattgatgt tggacgagtc    660
ggaatcgcag accgatacca ggatcttgcc atcctatgga actgcctcgg tgagttttct    720
ccttcattac agaaacggct ttttcaaaaa tatggtattg ataatcctga tatgaataaa    780
ttgcagtttc atttgatgct cgatgagttt ttctaa                             816
```

<210> SEQ ID NO 15
<211> LENGTH: 589
<212> TYPE: DNA
<213> ORGANISM: Artificial Sequence
<220> FEATURE:
<223> OTHER INFORMATION: pUC19 origin of replication

<400> SEQUENCE: 15

```
ttgagatcct ttttttctgc gcgtaatctg ctgcttgcaa acaaaaaaac caccgctacc     60
agcggtggtt tgtttgccgg atcaagagct accaactctt tttccgaagg taactggctt    120
cagcagagcg cagataccaa atactgttct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga tttttgtgat gctcgtcagg ggggcggagc ctatggaaa               589
```

TRANSGENE CASSETTES, AAV VECTORS, AND AAV VIRAL VECTORS FOR EXPRESSION OF HUMAN CODON-OPTIMIZED CSTB

CROSS REFERENCE TO RELATED APPLICATIONS

This application claims the benefit of U.S. Provisional Application No. 63/058,038, filed Jul. 29, 2020, which is incorporated by reference herein in its entirety for all purposes.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Jul. 15, 2021, is named "426871-000217 seq id" and is about 15 KB in size.

BACKGROUND

Unverricht-Lundborg disease (ULD, EPM1; OMIM 254800) is an inherited form of progressive myoclonus epilepsy (PME) which is characterized by myoclonus, epilepsy, and progressive neurologic deterioration of varying degrees. It is the most common of the rare genetically heterogeneous progressive myoclonic epilepsies. Although its worldwide prevalence is unknown, approximately 4 in 100,000 people are affected in Finland, where its higher incidence occurs. It is also more commonly encountered in western Mediterranean countries; therefore, it is also known as Baltic myoclonus and Mediterranean myoclonus. ULD is caused by mutations in the CSTB gene and inheritance is autosomal recessive. CSTB encodes cystatin B, a cysteine protease inhibitor. The most common mutation is a dodecamer repeat expansion in the CSTB gene (upstream to promoter). Patients usually retain ~10% of cystatin B activity. Despite some progress in understanding the biological function of cystatin B, the disease mechanism remains elusive. To better understand the disease, a cystatin B deficient mouse model had been created and characterized by Pennacchio et al., *Nat Genet,* 20(3), 251-258 (1998). This mouse model recapitulates human disease and provides insight into therapies.

Clinically, ULD is characterized by the triad of stimulus-sensitive myoclonus, epilepsy and progressive neurologic deterioration like other genetic myoclonic epilepsies, and patients are healthy before prior to disease onset. Affected individuals usually begin showing signs and symptoms of the disorder between the ages of 6 and 18. Early symptoms include involuntary muscle jerking or twitching (stimulus-sensitive myoclonus) and tonic-clonic or grand mal seizures. Over time, the myoclonic episodes may become severe enough to interfere with walking and other everyday activities. Additionally, ULD patients develop ataxia, lack of coordination, intention tremor, and dysarthria. These patients can also develop emotional sensitivity, depression, and a mild to moderate impairment of cognitive and intellectual performance over time.

The progression of the disease is slow, and patients usually maintain normal cognitive functioning for a long time with slow intellectual decline spanning 10-20 years. ULD patients typically live into adulthood. There is no targeted or disease-modifying therapy available. Currently available treatments including the antiepileptics that lessen the severity of myoclonus and the frequency of seizures, and psychosocial support aim to control symptoms and increase the quality of life. The overall outcome in adults ranges from independent active life with minimal impairment to severe disability and wheelchair-bound or even bedridden patients. Depending on the severity of the condition and a person's response to treatment, life expectancy may be normal.

In the absence of targeted therapy available for ULD, the current approaches aim to control symptoms and increase quality of life through lessening the severity of myoclonus and the frequency of seizures, as well as psychosocial support. There is still an unmet need for the development and test of a gene replacement therapy for ULD.

SUMMARY

Provided herein are gene expression cassettes designed to drive expression of a CSTB gene, such as a human codon optimized CSTB gene. Expression cassettes can be used for research and to test gene replacement therapy for genetic disorders involving a CSTB gene. Expression cassettes can also be used to treat diseases resulting from CSTB deficiencies, such as ULD.

The present disclosure provides an expression cassette comprising: SEQ ID NO:9; SEQ ID NO:3, and SEQ ID NO:9; or SEQ ID NO:2, SEQ ID NO:3, SEQ ID NO:9, SEQ ID NO:10, SEQ ID NO:11, SEQ ID NO:13, and SEQ ID NO:14.

The present disclosure provides an expression cassette comprising SEQ ID NO:9, one or more promoters, and one or more terminal repeats, or combinations thereof.

One or more promoters can comprise SEQ ID NO:3, and one or more terminal repeats can comprise SEQ ID NO:2 and/or SEQ ID NO:11. An expression cassette can comprise SEQ ID NO:1.

The present disclosure provides a vector or vectors comprising an expression cassette of comprising: SEQ ID NO:9; SEQ ID NO:3, and SEQ ID NO:9; SEQ ID NO:2, SEQ ID NO:3, SEQ ID NO:9, SEQ ID NO:10, SEQ ID NO:13, and SEQ ID NO:14; or SEQ ID NO:9, one or more promoters, and one or more terminal repeats, or combinations thereof.

The present disclosure provides an isolated nucleic acid molecule as set forth in SEQ ID NO:1 or SEQ ID NO:9.

The present disclosure provides a recombinant adeno-associated virus (rAAV) vector comprising in 5' to 3' direction: a first AAV inverted terminal repeat (ITR) sequence; a promoter sequence; a transgene nucleic acid molecule, wherein the transgene nucleic acid molecule comprises a nucleic acid sequence encoding for a CSTB polypeptide; a polyA sequence; and a second AAV ITR sequence.

A transgene nucleic acid molecule encoding for a CSTB polypeptide can comprise a codon optimized nucleic acid sequence encoding for a CSTB polypeptide. A codon optimized nucleic acid sequence encoding for a CSTB polypeptide can comprise the nucleic acid sequence set forth in SEQ ID NO:9. A codon optimized nucleic acid sequence encoding for a CSTB polypeptide can exhibit at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence.

A first AAV ITR sequence can comprise the nucleic acid sequence set forth in SEQ ID NO:2. A second AAV ITR sequence can comprise the nucleic acid sequence set forth in SEQ ID NO:11.

A promoter sequence can comprise a Rous sarcoma virus (RSV) LTR promoter (optionally with the RSV enhancer), a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a CAG promoter, a hybrid chicken beta-actin promoter, an MeCP2 promoter, an EF1 promoter, a ubiquitous chicken β-actin hybrid (CBh) promoter, a U1a promoter, a U1b promoter, an MeCP2 promoter, an MeP418 promoter, an MeP426 promoter, a minimal MeCP2 promoter, a VMD2 promoter, an mRho promoter, EFla promoter, Ubc promoter, human β-actin promoter, TRE promoter, Ac5 promoter, Polyhedrin promoter, CaMKIIa promoter, Gal1 promoter, TEF1 promoter, GDS promoter, ADH1 promoter, Ubi promoter, or α-1-antitrypsin (hAAT) promoter. A promoter sequence can comprise the nucleic acid sequence set forth in SEQ ID NO:3. A promoter sequence can comprise the nucleic acid sequence set forth in SEQ ID NO:5.

A polyA sequence can comprise the nucleic acid sequence set forth in SEQ ID NO:10.

An rAAV vector can comprise, in the 5' to 3' direction: a first AAV ITR sequence comprising the nucleic acid sequence set forth in SEQ ID NO:2; a promoter sequence comprising the nucleic acid sequence set forth in SEQ ID NO:3; a transgene nucleic acid molecule, wherein the transgene nucleic acid molecule comprises a nucleic acid sequence encoding for a CSTB polypeptide, wherein the nucleic acid sequence encoding for a CSTB polypeptide comprises the nucleic acid sequence set forth in SEQ ID NO:9; a polyA sequence comprising the nucleic acid sequence set forth in SEQ ID NO:10; and a second AAV ITR sequence comprising the nucleic acid sequence set forth in SEQ ID NO:11. An rAAV vector can comprise the nucleic acid sequence set forth in SEQ ID NO:1.

An rAAV viral vector can comprise: an AAV capsid protein; and any of the rAAV vectors described herein.

An AAV capsid protein can comprise an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein. An AAV capsid protein can be an AAV9 capsid protein.

The present disclosure provides a pharmaceutical composition comprising any of the rAAV viral vector described herein; and at least one pharmaceutically acceptable excipient and/or additive.

The present disclosure provides a method for treating a subject having a disease and/or disorder involving a CSTB gene, the method comprising administering to the subject at least one therapeutically effective amount of any of the rAAV viral vector or pharmaceutical compositions described herein.

A disease and/or disorder involving the CSTB gene can be Unverricht-Lundborg disease (ULD). An rAAV viral vector or a pharmaceutical composition can be administered to the subject at a dose ranging from about $10^{11}$ to about $10^{18}$ viral vector particles. An rAAV viral vector or pharmaceutical composition can be administered to the subject at a dose ranging from about $10^{13}$ to about $10^{16}$ viral vector particles. An rAAV viral vector or pharmaceutical composition can be administered to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. An rAAV viral vector or pharmaceutical composition can be administered intrathecally.

An rAAV viral vector can reduce cerebellar granular cell apoptosis in the subject. An rAAV viral vector can reduce early-onset, neuroinflammation, late-onset neuroinflammation or both early-onset and late-onset neuroinflammation in the subject. Neuroinflammation can be characterized by an increased expression in immune marker genes selected from the group consisting of CXCL1, CXCL10, CXCL13, GFAP, IBA1, or a combination thereof. An rAAV viral vector can prevent development of ataxia and/or improve motor coordination in the subject.

Any of the rAAV viral vectors or pharmaceutical compositions described herein can be for use in treating a disease and/or disorder involving a CSTB gene in a subject in need thereof.

A disease and/or disorder involving the CSTB gene can be Unverricht-Lundborg disease (ULD). An rAAV viral vector or pharmaceutical composition can be for administration to the subject at a dose ranging from about $10^{11}$ to about $10^{18}$ viral vector particles. An rAAV viral vector or pharmaceutical composition can be for administration to the subject at a dose ranging from about $10^{13}$ to about $10^{16}$ viral vector particles. An rAAV viral vector or pharmaceutical composition can be for administration to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. An rAAV viral vector or pharmaceutical composition can be for administration intrathecally.

Any of the above aspects, or any other aspect described herein, can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the appended claims. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

FIG. 2A shows brain CSTB western blots in cohort 1. FIG. 2B shows brain CSTB western blots in cohort 2. FIG. 2C shows brain CSTB western blots in cohort 3.

FIG. 3A shows a representative image of CSTB expressing cells in cohort 1. FIG. 3B shows a representative image of CSTB expressing cells in cohort 2.

FIG. 3C shows a representative image of CSTB expressing cells in cohort 3.

FIG. 4A shows a representative micrograph of TUNEL-stained cerebella in a PBS treated mouse. FIG. 4B shows a representative micrograph of TUNEL-stained cerebella in a AAV-CSTB treated mouse. FIG. 4C shows a representative micrograph of TUNEL-stained cerebella in a wild-type mouse used as control. FIG. 4D shows a bar graph of the quantification of TUNEL positive nuclei in the cerebellum. Data are mean±SEM. (N=~10-15 for each group).

FIG. 5A is a graph bar showing the relative mRNA expression of Cxcl1. FIG. 5B is a graph bar showing the relative mRNA expression of Cxcl10. FIG. 5C is a graph bar showing the relative mRNA expression of Cxcl13. FIG. 5D is a graph bar showing the relative mRNA expression of Gfap. FIG. 5E is a graph bar showing the relative mRNA expression of Iba1. All data are presented as mean±SEM. Significance levels are indicated as *, $p<0.05$; , $p<0.01$; *, $p<0.001$, ****, and $p<0.0001$. (N=~10-15 for each group).

FIG. 6A is a graph bar showing the analysis of motor coordination using stationary rod in cohort 1. FIG. 6B is a graph bar showing the analysis of motor coordination using accelerating (2 RPM) rod in cohort 1. FIG. 6C is a graph bar showing the analysis of motor coordination using stationary rod in cohort 2. FIG. 6D is a graph bar showing the analysis of motor coordination using accelerating (2 RPM) rod in cohort 2.

FIG. 7A is a graph bar showing the relative mRNA expression of Cxcl1 in cohort 2. FIG. 7B is a graph bar showing the relative mRNA expression of Cxcl10 in cohort 2. FIG. 7C is a graph bar showing the relative mRNA expression of Cxcl13 in cohort 2. FIG. 7D is a graph bar showing the relative mRNA expression of Gfap in cohort 2. FIG. 7E is a graph bar showing the relative mRNA expression of Iba1 in cohort 2. FIG. 7F is a graph bar showing the relative mRNA expression of Cxcl1 in cohort 3. FIG. 7G is a graph bar showing the relative mRNA expression of Cxcl10 in cohort 3. FIG. 7H is a graph bar showing the relative mRNA expression of Cxcl13 in cohort 3. FIG. 7I is a graph bar showing the relative mRNA expression of Gfap in cohort 3. FIG. 7J is a graph bar showing the relative mRNA expression of Iba1 in cohort 3. All data are presented as mean±SEM. Significance levels are indicated as *, $p<0.05$; , $p<0.01$; *, $p<0.001$, ****, and $p<0.0001$. (N=~10-15 for each group).

FIGS. 8A-8C show the effect of AAV-CSTB treatment on brain weight loss by analyzing milligram of total hemisphere in wild-type control, PBS or AAV-CSTB treated mice. FIG. 8A is a graph bar showing brain weight in cohort 1. FIG. 8B is a graph bar showing brain weight in cohort 2. FIG. 8C is a graph bar showing brain weight in cohort 3.

DETAILED DESCRIPTION

Figure 1:
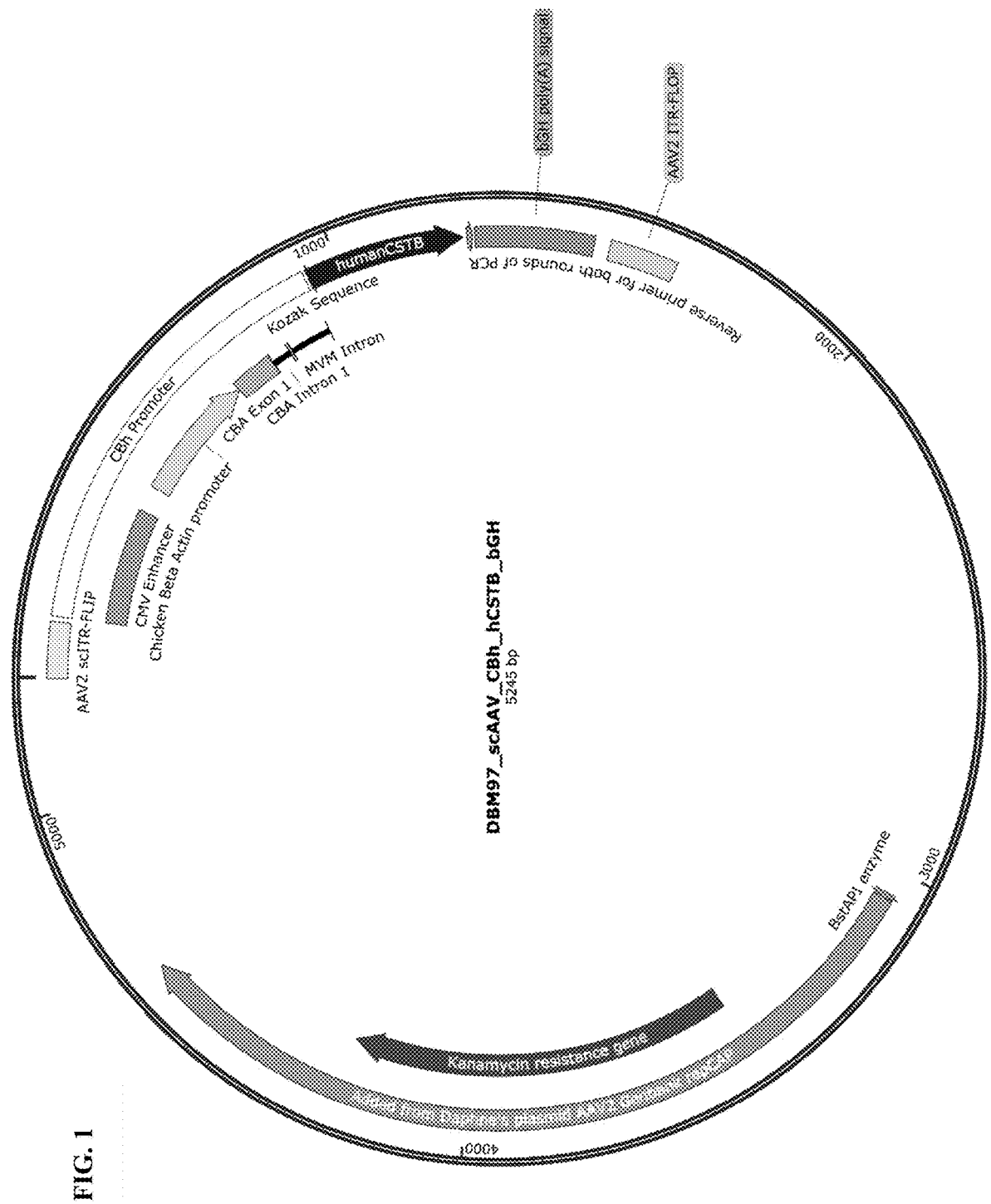
FIG. 1 is a schematic representation of the plasmid map of CBh-hCSTB-bGHpA.

The present disclosure provides, inter alia, isolated polynucleotides, expression cassettes, recombinant adeno-associated virus (rAAV) vectors, and rAAV viral vectors comprising transgene nucleic acid molecules encoding for CSTB polypeptides. The present disclosure also provides methods of manufacturing these isolated polynucleotides, expression cassettes, rAAV vectors, and rAAV viral vectors, as well as their use to deliver transgenes to treat or prevent a disease or disorder, including diseases associated with loss and/or misfunction of an CSTB gene.

A gene expression cassette can express a functional CSTB protein in cells receiving the cassette. A cassette can contain, for example, a CBh (CMV and chicken beta actin, CBA) hybrid promoter, which can drive strong, long-term and ubiquitous expression of a codon-optimized CSTB gene in all tissue types. Additionally, a CSTB nucleic acid molecule can be codon-optimized to facilitate optimal CSTB expression and stability. Thus, a sequence of a CSTB nucleic acid molecule can be non-naturally occurring and the combination of the CSTB nucleic acid molecule with cis-acting regulatory elements (e.g., promoter and polyA) represents a unique design optimal for treating CSTB deficiency (ULD).

The compositions provided herein solve the problem of a lack of reagents to study the effects of gene replacement in CSTB genetic disorders. The delivery of a functional CSTB gene to CSTB-deficient patients can be therapeutic, which represents a transformative treatment to address unmet medical needs of these patients.

CSTB encodes cystatin B, a protein of the cystatin superfamily, which encompasses proteins that contain multiple cystatin-like sequences, conferring to some of the members an active cysteine protease inhibitor activity. There are three inhibitory families in the superfamily, including the type 1 cystatins (stefins), type 2 cystatins and kininogens. CSTB encodes a stefin, which functions as an intracellular thiol protease inhibitor. Cystatin B can form dimer stabilized by noncovalent forces, and inhibit papain and cathepsins L, H and B. Cystatin B plays a role in protecting against the proteases leaking from lysosomes.

The mechanism of action behind the genetic defect in CSTB gene and the development of Unverricht-Lundborg disease is not clearly known but could be very similar to another theory of epilepsy progression known as kindling. Cystatin B could be linked to the production of inhibitory neurons known as GABAergic neurons; and mutations of the CSTB gene lead to a decrease in the number of inhibitory neurons. The lack of inhibition makes the cells in the brain, particularly the hippocampus, more excitable. The increase in excitability could be the cause the myoclonic jerks and tonic-clonic seizures in patients with ULD. Cystatin B plays a "protecting" role in the brain, and would normally, after a seizure, prevent neurons from dying due to toxic levels of neurotransmitters. The absence of cystatin B is responsible for the death of affected neurons, leading to a damaged portion of the brain. This damage coupled with the increased excitability of the cells then leads to more damage, which is what makes Unverricht-Lundborg disease progressive.

The constructs described herein can be delivered to patients using any suitable gene therapy methodology such that one or more symptoms of the disease is reduced or eliminated.

Expression Cassettes

Expression cassettes can be circular or linear nucleic acid molecules. In some cases, an expression cassette is delivered to cells (e.g., a plurality of different cells or cell types including target cells or cell types and/or non-target cell types) in a vector (e.g., an expression vector). As discussed in greater detail below, a vector can be an integrating or non-integrating vector, referring to the ability of the vector to integrate the expression cassette and/or transgene into a genome of a cell. Either an integrating vector or a non-integrating vector can be used to deliver an expression cassette containing a gene operably linked to a regulatory element. Examples of vectors include, but are not limited to, (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs); episomal vectors; transposons (e.g., PiggyBac); and (b) viral vectors such as retroviral vectors, lentiviral vectors, adenoviral vectors, and AAV vectors, which are discussed in greater detail below. Viruses have several advantages for delivery of nucleic acids, including high infectivity and/or tropism for certain target cells or tissues. In some cases, a virus is used to deliver a nucleic acid molecule or expression cassette comprising one or more regulatory elements, as described herein below, operably linked to a gene.

Isolated Polynucleotides Comprising Transgene Sequences

Provided herein are isolated expression cassettes, vectors, and polynucleotides comprising at least one transgene nucleic acid molecule.

In some aspects, a transgene nucleic acid molecule can comprise a nucleic acid sequence encoding a CSTB polypeptide or at least one fragment thereof. CSTB is encoded by the CSTB gene in the human genome. Thus, a transgene nucleic acid molecule can comprise, consist essentially of, or consist of an CSTB sequence, or any fragment thereof. In some aspects, a transgene nucleic acid molecule can comprise a nucleic acid sequence encoding a biological equivalent of a CSTB polypeptide.

In some aspects, a nucleic acid molecule encoding a CSTB polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence set forth in SEQ ID NO:9. A nucleic acid sequence encoding a CSTB polypeptide can be referred to as a CSTB sequence or CSTB nucleic acid molecule.

In some aspects, a nucleic acid sequence encoding a CSTB polypeptide can be a codon optimized nucleic acid sequence that encodes for a CSTB polypeptide. A codon optimized nucleic acid sequence encoding a CSTB polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wild-type human nucleic acid sequence encoding a CSTB polypeptide.

SEQ ID NO:9 is a unique codon optimized nucleic acid sequence that encodes for a CSTB polypeptide. In some aspects, a codon optimized nucleic acid sequence encoding a CSTB polypeptide, such as those put forth in SEQ ID NO:9, can comprise no donor splice sites. In some aspects, a codon optimized nucleic acid sequence encoding a CSTB polypeptide can comprise no more than about one, or about two, or about three, or about four, or about five, or about six, or about seven, or about eight, or about nine, or about ten donor splice sites. In some aspects, a codon optimized nucleic acid sequence encoding a CSTB polypeptide comprises at least one, or at least two, or at least three, or at least four, or at least five, or at least six, or at least seven, or at least eight, or at least nine, or at least ten fewer donor splice sites as compared to the wild-type human nucleic acid sequence encoding the CSTB polypeptide. Without wishing to be bound by theory, the removal of donor splice sites in the codon optimized nucleic acid sequence can unexpectedly and unpredictably increase expression of the CSTB polypeptide in vivo, as cryptic splicing is prevented. Moreover, cryptic splicing can vary between different subjects, meaning that the expression level of the CSTB polypeptide comprising donor splice sites can unpredictably vary between different subjects. Such unpredictability is undesirable in the context of human therapy. Accordingly, a codon optimized nucleic acid sequence, such as shown in SEQ ID NO:9, which lacks known donor splice sites, can unexpectedly and surprisingly allow for increased expression of the CSTB polypeptide in human subjects and regularizes expression of the CSTB polypeptide across different human subjects.

In some aspects, a codon optimized nucleic acid sequence encoding a CSTB polypeptide, such as those put forth in SEQ ID NO:9, can have a GC content that differs from the GC content of the wild-type human nucleic acid sequence encoding the CSTB polypeptide. In some aspects, the GC content of a codon optimized nucleic acid sequence encoding a CSTB polypeptide is more evenly distributed across the entire nucleic acid sequence, as compared to the wild-type human nucleic acid sequence encoding the CSTB polypeptide. Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature can result in unexpectedly increased expression of the codon optimized nucleic acid in a human subject, as transcription and/or translation of the nucleic acid sequence occurs with less stalling of the polymerase and/or ribosome.

In some aspects, a codon optimized nucleic acid sequence encoding a CSTB polypeptide, such as SEQ ID NO:9, can have fewer repressive microRNA target binding sites as compared to the wild-type human nucleic acid sequence encoding the CSTB polypeptide. In some aspects, a codon optimized nucleic acid sequence encoding a CSTB polypeptide can have at least one, or at least two, or at least three, or at least four, or at least five, or at least six, or at least seven, or at least eight, or at least nine, or at least ten, or at least ten fewer repressive microRNA target binding sites as compared to the wild-type human nucleic acid sequence encoding the CSTB polypeptide. Without wishing to be bound by theory, by having fewer repressive microRNA target binding sites, the codon optimized nucleic acid sequence encoding a CSTB polypeptide can unexpectedly exhibit increased expression in a human subject.

In some aspects, a codon optimized nucleic acid sequence encoding a CSTB polypeptide exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence encoding a CSTB polypeptide.

In an embodiment, an expression cassette can comprise a codon optimized CSTB polynucleotide such as SEQ ID NO:9. An expression cassette can further comprise, for example, a 5' terminal repeat, a 3' terminal repeat, or a combination of both. A terminal repeat can be suitable for use in an AAV vector, which is discussed in greater detail below. In an example, a 5' terminal repeat is shown in SEQ ID NO:2 or SEQ ID NO:11.

An expression cassette can further comprise a promoter to drive expression of the CSTB polynucleotide. The promoter can be, for example, a CBH promoter, but any suitable promoter can be used. In an embodiment a promoter is shown in SEQ ID NO:3. An expression cassette can further comprise a selectable marker such as an antibiotic resistance marker. In an embodiment, an expression cassette comprises and kanamycin resistance polynucleotide (e.g., SEQ ID NO:14). An expression cassette can further comprise a promoter to drive expression of the antibiotic resistance polynucleotide. The promoter can be, for example, a AmpR promoter, but any suitable promoter can be used. In an embodiment a promoter is shown in SEQ ID NO:13.

In an embodiment an expression cassette can comprise SEQ ID NO:1. In an embodiment, an expression cassette can comprise SEQ ID NO:2, 3, 9, 10, 13, 14, or any combination thereof.

All elements described herein (e.g., terminal repeat, promoters, selectable marker, and codon optimized polynucleotide) for incorporation into vectors and expression cassettes are interchangeable, and therefore can all be combined in any manner. The expression cassettes/vectors described herein are only exemplary, and all the expression cassette/vector that can be generated comprising any combination of the described elements are included herein.

An embodiment provides an expression cassette or vector comprising SEQ ID NO:3, and SEQ ID NO:9. SEQ ID NO:2, SEQ ID NO:3, SEQ ID NO:9, SEQ ID NO:10, SEQ ID NO:11, SEQ ID NO:13, and SEQ ID NO:14 can be operably linked to one another.

An embodiment comprises an expression cassette comprising SEQ ID NO:1. An expression cassette can be present in a vector and the vector can be delivered to a patient. Provided herein are methods of treating a CSTB deficiency comprising delivering the expression cassettes or vectors to a patient.

A embodiment provides an expression cassette or vector that comprises SEQ ID NO:3 SEQ ID NO:4, SEQ ID NO:5, SEQ ID NO:6, SEQ ID NO:7, and SEQ ID NO:8.

Methods for preparing polynucleotides operably linked to expression control sequences and/or regulatory elements and expressing polypeptides in a host cell are well-known in the art. See, e.g., U.S. Pat. No. 4,366,246.

Vectors

As used herein, the term "vector" refers to a nucleic acid comprising, consisting essentially of, or consisting of an intact replicon such that the vector can be replicated when placed within a cell, for example by a process of transfection, infection, or transformation. It is understood in the art that once inside a cell, a vector can replicate as an extrachromosomal (episomal) element or can be integrated into a host cell chromosome. Vectors can include nucleic acids derived from retroviruses, adenoviruses, herpesvirus, baculoviruses, modified baculoviruses, papovaviruses, or otherwise modified naturally-occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising, consisting essentially of, or consisting of DNA condensed with cationic polymers such as heterogeneous polylysine, defined-length oligopeptides, and polyethyleneimine, in some cases contained in liposomes; and the use of ternary complexes comprising, consisting essentially of, or consisting of a virus and polylysine-DNA.

With respect to general recombinant techniques, vectors that contain both a promoter and a cloning site into which a polynucleotide can be operably linked can be used. Such vectors are capable of transcribing RNA in vitro or in vivo. To optimize expression and/or in vitro transcription, it can be necessary to remove, add or alter 5' and/or 3' untranslated portions of cloned transgenes to eliminate extra, potential inappropriate alternative translation initiation codons or other sequences that can interfere with or reduce expression, either at the level of transcription or translation. Alternatively, consensus ribosome binding sites can be inserted immediately 5' of the start codon to enhance expression.

Viral Vectors

A "viral vector" is defined as a recombinantly produced virus or viral particle that contains a polynucleotide to be delivered into a host cell, either in vivo, ex vivo or in vitro. Examples of viral vectors include retroviral vectors, AAV vectors, lentiviral vectors, adenovirus vectors, alphavirus vectors and the like. Alphavirus vectors, such as Semliki Forest virus-based vectors and Sindbis virus-based vectors, have also been developed for use in gene therapy and immunotherapy. See, e.g., Schlesinger and Dubensky (1999) Curr. Opin. Biotechnol. 5: 434-439 and Ying, et al. (1999) Nat. Med. 5(7): 823-827.

Techniques contemplated herein for gene therapy of somatic cells include delivery via a viral vector (e.g., retroviral, adenoviral, AAV, helper-dependent adenoviral systems, hybrid adenoviral systems, herpes simplex, pox virus, lentivirus, and Epstein-Barr virus), and non-viral systems, such as physical systems (naked DNA, DNA bombardment, electroporation, hydrodynamic, ultrasound, and magnetofection), and chemical system (cationic lipids, different cationic polymers, and lipid polymers).

The cloning capacity of vectors or viral expression vectors is a particular challenge for expression of large transgenes. For example, AAV vectors typically have a packaging capacity of 4.8 kb, lentiviruses typically have a capacity of 8 kb, adenoviruses typically have a capacity of 7.5 kb and alphaviruses typically have a capacity of 7.5 kb. Some viruses can have larger packaging capacities, for example herpesvirus can have a capacity of >30 kb and vaccinia a capacity of 25 kb. Advantages of using AAV for gene therapy include low pathogenicity, very low frequency of integration into the host genome, and the ability to infect dividing and non-dividing cells.

Viral gene therapy vectors or gene delivery vectors can have the ability to be reproducible and stably propagated and purified to high titers; to mediate targeted delivery (e.g., to deliver the transgene specifically to a tissue or organ of interest without widespread vector dissemination elsewhere or off-target delivery); and to mediate gene delivery and/or transgene expression without inducing harmful side effects or off-target effects.

The term "adeno-associated virus" or "AAV" as used herein refers to a member of the class of viruses associated with this name and belonging to the genus Dependoparvovirus, family Parvoviridae. Adeno-associated virus is a single-stranded DNA virus that grows in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized in the future because the various serotypes are quite closely related, both structurally and functionally, even at the genetic level. See, for example, Blacklowe, 1988, pp. 165-174 of Parvoviruses and Human Disease, J. R. Pattison, ed.; and Rose, Comprehensive Virology 3: 1-61 (1974). For example, all AAV serotypes apparently exhibit very similar replication properties mediated by homologous rep genes; and all have three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. Multiple serotypes of this virus are known to be suitable for gene delivery; all known serotypes can infect cells from various tissue types. At least 11 sequentially numbered AAV serotypes are known in the art. Non-limiting exemplary serotypes useful in the methods disclosed herein include any of the 11 serotypes, e.g., AAV2, AAV8, AAV9, or variant serotypes, e.g., AAV-DJ and AAV PHP.B. The AAV particle comprises, consists essentially of, or consists of three major viral proteins: VPI, VP2 and VP3. In some aspects, the AAV refers to the serotype AAV1, AAV2, AAV4, AAV5, AAV6, AAV7, AAV8, AAV9, AAV10, AAV11, AAV12, AAV13, AAVPHP.B, AAVrh74 or AAVrh.10.

Exemplary adeno-associated viruses and recombinant adeno-associated viruses include, but are not limited to all serotypes (e.g., AAV1, AAV2, AAV3, AAV4, AAV5, AAV6, AAV7, AAV8, AAV9, AAV10, AAV11, AAV12, AAV13, AAVPHP.B, AAVrh74 and AAVrh.10). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03, AAV-KP-1 (described in detail in Kerun et al. JCI Insight, 2019; 4(22): e131610) and AAV-NP59 (described in detail in Paulk et al. Molecular Therapy, 2018; 26(1): 289-303).

AAV Structure and Function

AAV is a replication-deficient parvovirus, the single-stranded DNA genome of which is about 4.7 kb in length, including two 145-nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_I829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928. U.S. Pat. No. 9,434,928 also provides the sequences of the capsid proteins and a self-complementary genome. In one aspect, an AAV genome is a self-complementary genome. Cis-acting sequences directing viral DNA replication (rep), encapsidation/packaging, and host cell chromosome integration are contained within AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome.

The cap gene is expressed from the p40 promoter and encodes the three capsid proteins, VPI, VP2, and VP3. Alternative splicing and non-consensus translational start sites are responsible for the production of the three related capsid proteins. More specifically, after the single mRNA from which each of the VP1, VP2 and VP3 proteins are translated is transcribed, it can be spliced in two different manners: either a longer or shorter intron can be excised, resulting in the formation of two pools of mRNAs: a 2.3 kb- and a 2.6 kb-long mRNA pool. The longer intron is often preferred and thus the 2.3-kb-long mRNA can be called the major splice variant. This form lacks the first AUG codon, from which the synthesis of VP1 protein starts, resulting in a reduced overall level of VP1 protein synthesis. The first AUG codon that remains in the major splice variant is the initiation codon for the VP3 protein. However, upstream of that codon in the same open reading frame lies an ACG sequence (encoding threonine) which is surrounded by an optimal Kozak (translation initiation) context. This contributes to a low level of synthesis of the VP2 protein, which is actually the VP3 protein with additional N terminal residues, as is VP1, as described in Becerra S P et al., (December 1985). "Direct mapping of adeno-associated virus capsid proteins B and C: a possible ACG initiation codon". Proceedings of the National Academy of Sciences of the United States of America. 82 (23): 7919-23, Cassinotti Petal., (November 1988). "Organization of the adeno-associated virus (AAV) capsid gene: mapping of a minor spliced mRNA coding for virus capsid protein 1". Virology. 167 (1): 176-84, Muralidhar S et al., (January 1994). "Site-directed mutagenesis of adeno-associated virus type 2 structural protein initiation codons: effects on regulation of synthesis and biological activity". Journal of Virology. 68 (1): 170-6, and Trempe J P, Carter B J (September 1988). "Alternate mRNA splicing is required for synthesis of adeno-associated virus VP1 capsid protein". Journal of Virology. 62 (9): 3356-63, each of which is herein incorporated by reference. A single consensus polyA site is located at map position 95 of the AAV genome. The life cycle and genetics of AAV are reviewed in Muzyczka, Current Topics in Microbiology and Immunology, 158: 97-129 (1992).

Each VP1 protein contains a VP1 portion, a VP2 portion and a VP3 portion. The VP1 portion is the N-terminal portion of the VP1 protein that is unique to the VP1 protein. The VP2 portion is the amino acid sequence present within the VP1 protein that is also found in the N-terminal portion of the VP2 protein. The VP3 portion and the VP3 protein have the same sequence. The VP3 portion is the C-terminal portion of the VP1 protein that is shared with the VP1 and VP2 proteins.

The VP3 protein can be further divided into discrete variable surface regions I-IX (VR-I-IX). Each of the variable surface regions (VRs) can comprise or contain specific amino acid sequences that either alone or in combination with the specific amino acid sequences of each of the other VRs can confer unique infection phenotypes (e.g., decreased antigenicity, improved transduction and/or tissue-specific tropism relative to other AAV serotypes) to a particular serotype as described in DiMatta et al., "Structural Insight into the Unique Properties of Adeno-Associated Virus Serotype 9" J. Virol., Vol. 86 (12): 6947-6958, June 2012, the contents of which are incorporated herein by reference.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) can be replaced with foreign DNA to generate AAV vectors. The rep and cap proteins can be provided in trans. Another significant feature of AAV is that it is an extremely stable and hearty virus. It easily withstands the conditions used to inactivate adenovirus (56° to 65° C. for several hours), making cold preservation of AAV less critical. AAV can even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes comprise, consist essentially of, or consist of a nucleic acid molecule encoding a therapeutic protein (e.g., CSTB) and one or more AAV ITRs flanking the nucleic acid molecule. Production of pseudotyped rAAV is disclosed in, for example, WO2001083692. Other types of rAAV variants, for example rAAV with capsid mutations, are also contemplated. See, e.g., Marsic et al., Molecular Therapy, 22(11): 1900-1909 (2014). The nucleotide sequences of the genomes of various AAV serotypes are known in the art.

In one embodiment, an expression cassette can comprise a nucleic acid molecule comprising a codon-optimized CSTB gene. In one embodiment, the expression cassette is delivered to cells in a, for example, AAV9 vector.

AAV ITR Sequences

In some aspects, an AAV ITR sequence can comprise any AAV ITR sequence known in the art. In some aspects, an AAV ITR sequence can be an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence or an AAVrh.10 ITR sequence.

Thus, in some aspects, an AAV ITR sequence can comprise, consist essentially of, or consist of an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, or an AAVrh.10 ITR sequence.

In some aspects, an rAAV vector of the present disclosure can comprise, consist essentially of, or consist of AAV2 ITR sequences. In some aspects, an rAAV vector of the present disclosure can comprise, consist essentially of, or consist of AAV2 ITR sequences or a modified AAV2 ITR sequence.

In some aspects, an AAV2 ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:2.

In some aspects, a modified AAV2 ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:11

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:2 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:11.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:2 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:11.

In some aspects, the isolated polynucleotides comprising at least one transgene nucleic acid molecule described herein can be a recombinant AAV (rAAV) vector.

Recombinant AAV (rAAV) Vector

An "rAAV vector" refers to a vector comprising, consisting essentially of, or consisting of one or more transgene sequences and one or more AAV inverted terminal repeat sequences (ITRs). Such AAV vectors can be replicated and packaged into infectious viral particles when present in a host cell that provides the functionality of rep and cap gene products; for example, by transfection of the host cell. In some aspects, AAV vectors contain a promoter, at least one nucleic acid molecule that can encode at least one protein or RNA, and/or an enhancer and/or a terminator within the flanking ITRs that is packaged into the infectious AAV particle. The encapsidated nucleic acid portion can be referred to as the AAV vector genome. Plasmids containing rAAV vectors can also contain elements for manufacturing purposes, e.g., antibiotic resistance genes, origin of replication sequences etc., but these are not encapsidated and thus do not form part of the AAV particle.

In some aspects, an rAAV vector can comprise at least one transgene nucleic acid molecule. In some aspects, an rAAV vector can comprise at least one AAV inverted terminal (ITR) sequence. In some aspects, an rAAV vector can comprise at least one promoter sequence. In some aspects, an rAAV vector can comprise at least one enhancer sequence. In some aspects, an rAAV vector can comprise at least one polyA sequence. In some aspects, an rAAV vector can comprise at least one nucleic acid molecule encoding one or more reporter proteins.

In some aspects, an rAAV vector can comprise a first AAV ITR sequence, a promoter sequence, a transgene nucleic acid molecule, a polyA sequence, and a second AAV ITR sequence. In some aspects, an rAAV vector can comprise, in the 5' to 3' direction, a first AAV ITR sequence, a promoter sequence, a transgene nucleic acid molecule, a polyA sequence, and a second AAV ITR sequence.

In some aspects, an rAAV vector can comprise more than one transgene nucleic acid molecule. In some aspects, an rAAV vector can comprise at least two transgene nucleic acid molecules, such that the rAAV vector comprises a first transgene nucleic acid molecule and an at least second transgene nucleic acid molecule. In some aspects, the first and the at least second transgene nucleic acid molecule can comprise the same nucleic acid sequence. In some aspects, the first and the at least second transgene nucleic acid molecules can comprise different nucleic acid sequences. In some aspects, the first and the at least second transgene nucleic acid sequences can be adjacent to each other. Alternatively, the first and at least second transgene can be separated by about 5, 100, 500, 1,000 or more base pairs.

In some aspects, an rAAV vector can comprise more than one promoter sequence (e.g. 2, 3, 4, 5, 10 or more promoter sequences). In some aspects, an rAAV vector can comprise at least two promoter sequences, such that the rAAV vector comprises a first promoter sequence and an at least second promoter sequence. In some aspects, the first and the at least second promoter sequences can comprise the same sequence. In some aspects, the first and the at least second promoter sequences can comprise different sequences. In some aspects, the first and the at least second promoter sequences can be adjacent to each other. In some aspects wherein an rAAV vector also comprises a first transgene nucleic acid molecule and an at least second transgene nucleic acid molecule, the first promoter can be located upstream (5') of the first transgene nucleic acid molecule and the at least second promoter can be located between the first transgene nucleic acid molecule and the at least second transgene nucleic acid molecule, such that the at least second promoter is downstream (3') of the first transgene nucleic acid molecule and upstream (5') of the at least second transgene nucleic acid molecule.

Any of the preceding rAAV vectors can further comprise at least one enhancer (e.g. 1, 2, 3, 4, 5, 10 or more enhancers). The at least one enhancer can be located anywhere in the rAAV vector. In some aspects, the at least one enhancer can be located immediately upstream (5') of a promoter. Thus, an rAAV vector can comprise, in the 5' to 3' direction, a first AAV ITR sequence, an enhancer, a promoter sequence, a transgene nucleic acid molecule, a polyA sequence, and a second AAV ITR sequence. In some aspects, the at least one enhancer can be located immediately downstream (3') of a promoter. Thus, an rAAV vector can comprise, in the 5' to 3' direction, a first AAV ITR sequence, a promoter sequence, an enhancer, a transgene nucleic acid molecule, a polyA sequence, and a second AAV ITR sequence. In some aspects, the at least one enhancer can be located immediately downstream of a transgene nucleic acid molecule. Thus, an rAAV vector can comprise, in the 5' to 3' direction, a first AAV ITR sequence, a promoter sequence, a transgene nucleic acid molecule, an enhancer, a polyA sequence, and a second AAV ITR sequence.

Promoter Sequences and Enhancers

The term "promoters" and "promoter sequences" means control sequences that are a region of a polynucleotide sequence at which the initiation and rate of transcription of a coding sequence, such as a gene or a transgene, are controlled. Promoters can be constitutive, inducible, repressible, or tissue-specific, for example. Promoters can contain genetic elements at which regulatory proteins and molecules such as RNA polymerase and transcription factors can bind. Non-limiting exemplary promoters include Rous sarcoma virus (RSV) LTR promoter (optionally with the RSV enhancer), a cytomegalovirus (CMV) promoter, an SV40 promoter, a dihydrofolate reductase promoter, a β-actin promoter, a phosphoglycerol kinase (PGK) promoter, a U6 promoter, an H1 promoter, a ubiquitous chicken β-actin hybrid (CBh) promoter, a small nuclear RNA (U1a or U1b) promoter, an MeCP2 promoter, an MeP418 promoter, an MeP426 promoter, a minimal MeCP2 promoter, a VMD2 promoter, an mRho promoter, or an EF1 promoter.

Additional non-limiting exemplary promoters provided herein include, but are not limited to EFla, Ubc, human β-actin, CAG, TRE, Ac5, Polyhedrin, CaMKIIa, Gall, TEF1, GDS, ADH1, Ubi, and α-1-antitrypsin (hAAT). It is known in the art that the nucleotide sequences of such promoters can be modified in order to increase or decrease the efficiency of mRNA transcription. See, e.g., Gao et al. (2018) Mol. Ther.: Nucleic Acids 12: 135-145 (modifying TATA box of 7SK, U6 and H1 promoters to abolish RNA polymerase III transcription and stimulate RNA polymerase II-dependent mRNA transcription). Synthetically-derived promoters can be used for ubiquitous or tissue specific expression. Furthermore, virus-derived promoters, some of which are noted above, can be useful in the methods disclosed herein, e.g., CMV, HIV, adenovirus, and AAV promoters. In some aspects, a promoter is used together with at least one enhancer to increase the transcription efficiency. Non-limiting examples of enhancers include an interstitial retinoid-binding protein (IRBP) enhancer, an RSV enhancer, or a CMV enhancer.

In some aspects, a promoter sequence can comprise, consist essentially of, or consist of a Rous sarcoma virus (RSV) LTR promoter sequence (optionally with the RSV enhancer), a cytomegalovirus (CMV) promoter sequence, an SV40 promoter sequence, a dihydrofolate reductase promoter sequence, a β-actin promoter sequence, a phosphoglycerol kinase (PGK) promoter sequence, a U6 promoter sequence, an H1 promoter sequence, a ubiquitous chicken β-actin hybrid (CBh) promoter sequence, a small nuclear RNA (U1a or U1b) promoter sequence, an MeCP2 promoter sequence, an MeP418 promoter sequence, an MeP426 promoter sequence, a minimal MeCP2 promoter sequence, a VMD2 promoter sequence, an mRho promoter sequence, an EFI promoter sequence, an EFla promoter sequence, a Ubc promoter sequence, a human β-actin promoter sequence, a CAG promoter sequence, a TRE promoter sequence, an Ac5 promoter sequence, a Polyhedrin promoter sequence, a CaMKIIa promoter sequence, a Gal1 promoter sequence, a TEF1 promoter sequence, a GDS promoter sequence, an ADH1 promoter sequence, a Ubi promoter sequence or an α-1-antitrypsin (hAAT) promoter sequence.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter can be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) or synthetic techniques such that transcription of that gene is directed by the linked enhancer/promoter. Non-limiting examples of linked enhancer/promoter for use in the methods, compositions and constructs provided herein include a PDE promoter plus IRBP enhancer or a CMV enhancer plus U1a promoter. It is understood in the art that enhancers can operate from a distance and irrespective of their orientation relative to the location of an endogenous or heterologous promoter. It is thus further understood that an enhancer operating at a distance from a promoter is thus "operably linked" to that promoter irrespective of its location in the vector or its orientation relative to the location of the promoter.

As used throughout the disclosure, the term "operably linked" refers to the expression of a gene (i.e. a transgene) that is under the control of a promoter with which it is spatially connected. A promoter can be positioned 5' (upstream) or 3' (downstream) of a gene under its control. A promoter can be positioned 5'(upstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

In some aspects, a promoter sequence can comprise, consist essentially of, or consist of a CBh promoter sequence. A CBh promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:3.

In some aspects, a CBh promoter sequence can comprise, consist essentially of, or consist of a CMV enhancer, a CBA promoter, a CBA exon and a MVM intron. A CMV enhancer sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:4. A CBA promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:5. A CBA exon sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:7. A MVM intron sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:8.

In some aspects, plasmids or vectors can comprise a prokaryotic promoter. A prokaryotic promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:13.

Transgene Nucleic Acid Molecules

In some aspects, a transgene nucleic acid molecule can comprise a nucleic acid sequence encoding a CSTB polypeptide, or at least one fragment thereof. In some aspects, a transgene nucleic acid molecule can comprise a nucleic acid sequence encoding a biological equivalent of a CSTB polypeptide, or at least one fragment thereof.

In some aspects, a nucleic acid sequence encoding a CSTB polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to any one of the nucleic acid sequences put forth in SEQ ID NO:9. A nucleic acid sequence encoding a CSTB polypeptide can be referred to as a CSTB sequence.

In some aspects, a nucleic acid molecule encoding a CSTB polypeptide can be a codon optimized nucleic acid sequence that encodes for a CSTB polypeptide. A codon optimized nucleic acid sequence encoding a CSTB polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wild-type human nucleic acid sequence encoding the CSTB polypeptide.

SEQ ID NO:9 is a unique codon optimized nucleic acid sequence that encodes for a CSTB polypeptide.

In some aspects, a transgene nucleic acid molecule can comprise, consist essentially of, or consist of a nucleic acid sequence encoding a reporter protein. As used herein, a reporter protein is a detectable protein that is operably linked to a promoter to assay the expression (for example, tissue specificity and/or strength) of the promoter. In aspects, a reporter protein can be operably linked to a polypeptide. In aspects, reporter proteins can be used in monitoring DNA delivery methods, functional identification and characterization of promoter and enhancer elements, translation and transcription regulation, mRNA processing and protein: protein interactions. Non-limiting examples of a reporter protein are β-galactosidase; a fluorescent protein, such as, Green Fluorescent Protein (GFP) or Red Fluorescent Protein (RFP); luciferase; glutathione S-transferase; and maltose binding protein.

In some aspects, a transgene nucleic acid molecule can further comprise a nucleic acid sequence encoding a signal peptide.

PolyA Sequences

In some aspects, a polyadenylation (polyA) sequence can comprise any polyA sequence known in the art. Non-limiting examples of polyA sequences include, but are not limited to, an_MeCP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

Thus, a polyA sequence can comprise, consist essentially of, or consist of an MeCP2 polyA sequence, a retinol dehydrogenase 1 (RDH1) polyA sequence, a bovine growth hormone (bGH) polyA sequence, an SV40 polyA sequence, a SPA49 polyA sequence, a sNRP-TK65 polyA sequence, a sNRP polyA sequence, or a TK65 polyA sequence.

In some aspects, a polyA sequence can comprise, consist essentially of, or consist of an bGHpA sequence. In some aspects, an bGHpA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs:10.

Bacterial Plasmids

In some aspects, the rAAV vectors of the present disclosure can be contained within a bacterial plasmid to allow for propagation of the rAAV vector in vitro. Thus, the present disclosure provides bacterial plasmids comprising any of the rAAV vectors described herein. A bacterial plasmid can further comprise an origin of replication sequence. A bacterial plasmid can further comprise an antibiotic resistance gene. A bacterial plasmid can further comprise a prokaryotic promoter.

An exemplary schematic of a bacterial plasmid comprising an rAAV vector is shown in FIG. 1. In this non-limiting example, the rAAV vector in the bacterial plasmid comprises, in the 5' to 3' direction, a modified AAV2 ITR, a CBh promoter sequence, a transgene nucleic acid molecule comprising a codon-optimized nucleic acid sequence encoding a CSTB polypeptide, an bGHpA sequence and an AAV2 ITR.

In some aspects, a bacterial plasmid of the present disclosure can comprise, consist essentially of, or consist of the nucleic acid sequence set forth in SEQ ID NO:1, which is shown below. SEQ ID NO:1 is a 5245pb pscAAV CBh hCSTB. SEQ ID NO:1 includes SEQ ID NOs:2-15. SEQ ID NO:2 is an ITR derived from AAV2-FLIP, which has been mutated for the scGenome. SEQ ID NO:2 is present within SEQ ID NO:1 at nucleotides 1-105 and SEQ ID NO:2 is 105 bp in length. SEQ ID NO:3 is a CBh hybrid promoter. SEQ ID NO:3 is present within SEQ ID NO:1 at nucleotides 117-928 and SEQ ID NO:3 is 812 bp in length. SEQ ID NO:4 is a CMV enhancer. SEQ ID NO:4 is present withing SEQ ID NO:1 at nucleotides 117-410 and SEQ ID NO:4 is 304 bp in length. SEQ ID NO:5 is a CBA promoter. SEQ ID NO:5 is present within SEQ ID NO:1 at nucleotides 422-699 and SEQ ID NO:5 is 278 bp in length. SEQ ID NO:6 is a hybrid intron. SEQ ID NO:6 is present in SEQ ID NO:1 at nucleotides 700-928 and SEQ ID NO:6 is 229 bp in length. SEQ ID NO:7 is a CBA intron 1. SEQ ID NO:7 is present within SEQ ID NO:1 at nucleotides 794-836 and SEQ ID NO:7 is 43 bp in length. SEQ ID NO:8 is MVM intron. SEQ ID NO:8 is present within SEQ ID NO:1 at nucleotides 842-933 and SEQ ID NO:8 is 92 bp in length. SEQ ID NO:9 is hCSTB. SEQ ID NO:9 is present within SEQ ID NO:1 at nucleotides 935-1,251 and SEQ ID NO:9 is 317 bp in length. SEQ ID NO:10 is bovine growth hormone polyA. SEQ ID NO:10 is present within SEQ ID NO:1 at nucleotides 1,267-1,491 and SEQ ID NO:10 is 225 bp in length. SEQ ID NO:11 is an ITR derived from AAV2-FLOP, which has been mutated for the scGenome. SEQ ID NO:11 is present within SEQ ID NO:1 at nucleotides 1522-1666 and SEQ ID NO:11 is 145 bp in length. SEQ ID NO:12 is an M13 bacteriophage origin of replication. SEQ ID NO:12 is present within SEQ ID NO:1 at nucleotides 2,069-2,582 and SEQ ID NO:12 is 514 bp in length. SEQ ID NO:13 is an AmpR promoter. SEQ ID NO:13 is present within SEQ ID NO:1 at nucleotides 3,329-3,433 and SEQ ID NO:13 is 105 bp in length. SEQ ID NO:14 is KanR. SEQ ID NO:14 is present within SEQ ID NO:14 at nucleotides 3,434-4,249 and SEQ ID NO:14 is 816 bp in length. SEQ ID NO:15 is a pUC19 origin of replication. SEQ ID NO:15 is present within SEQ ID NO:1 at nucleotides 4,420-5,008 and SEQ ID NO:15 is 589 bp in length.

pscAAV_CBh_hCSTB (5,245 bp)

(SEQ ID NO: 1)
tgcgcgctcgctcgctcactgaggccgcccgggcaaagcccgggcgtcg ggcgacctttggtcgcccggcctcagtgagcgagcgagcgcgcagagag ggagtggggttcggtacccgttacataacttacggtaaatggcccgcct ggctgaccgcccaacgaccccgcccattgacgtcaataatgacgtatg ttcccatagtaacgccaatagggactttccattgacgtcaatgggtgga gtatttacggtaaactgcccacttggcagtacatcaagtgtatcatatg ccaagtacgccccctattgacgtcaatgacggtaaatggcccgcctggc attatgcccagtacatgaccttatgggactttcctacttggcagtacat ctacgtattagtcatcgctattaccatggtcgaggtgagccccacgttc tgcttcactctccccatctccccccctccccaccccaattttgtatt tatttattttttaattattttgtgcagcgatggggcggggggggggg ggggcgcgcgccaggcggggcggggcgggcgaggggcggggcgggcg aggcggagaggtgcggcggcagccaatcagagcggcgcgctccgaaagt ttccttttatggcgaggcggcggcggcggcggccctataaaaagcgaag cgcgcggcgggcgggagtcgctgcgacgctgccttcgccccgtgccccg ctccgccgccgcctcgcgccgcccgccccggctctgactgaccgcgtta ctcccacaggtgagcgggcgggacggcccttctcctccgggctgtaatt agctgagcaagaggtaagggtttaagggatggttggttggtggggtatt aatgtttaattacctggagcacctgcctgaaatcacttttttttcaggtt ggaACCGGTGCCACCATGATGTGCGGAGCCCCTTCAGCCACCCAACCCG

CCACTGCCGAGACACAGCATATTGCCGACCAAGTCCGGTCGCAGTTGGA

AGAAAAGGAAAACAAGAAATTCCCGGTGTTCAAGGCAGTGTCCTTCAAG

TCCCAAGTCGTGGCGGGGACTAATTACTTCATCAAAGTGCACGTCGGCG

ATGAGGACTTCGTGCATCTGCGCGTGTTTCAGTCCCTTCCGCACGAGAA

CAAGCCACTCACCCTGAGCAACTACCAGACCAACAAGGCTAAGCACGAC

GAACTGACCTACTTCTAAGCGGCCGCgcgcggatccctcgactgtgcct tctagttgccagccatctgttgtttgcccctcccccgtgccttccttga ccctggaaggtgccactcccactgtcctttcctaataaaatgaggaaat tgcatcgcattgtctgagtaggtgtcattctattctgggggtggggtg gggcaggacagcaaggggggaggattgggaagacaacagcaggcatgctg gggatgcggtgggctctatggcttctgaggcggaaagaaccagctacgc gtaggaaccctagtgatggagttggccactccctctctgcgcgctcgc tcgctcactgaggccgggcgaccaaaggtcgcccgacgcccgggctttg -continued cccgggcggcctcagtgagcgagcgagcgcgccagctggcgtaatagcg aagaggcccgcaccgatcgcccttcccaacagttgcgcagcctgaatgg cgaatggaattccagacgattgagcgtcaaaatgtaggtatttccatga gcgttttcctgttgcaatggctggcggtaatattgttctggatattac cagcaaggccgatagtttgagttcttctactcaggcaagtgatgttatt actaatcaaagaagtattgcgacaacggttaatttgcgtgatggacaga ctcttttactcggtggcctcactgattataaaaacacttctcaggattc tggcgtaccgttcctgtctaaaatcccttaatcggcctcctgtttagc tcccgctctgattctaacgaggaaagcacgttatacgtgctcgtcaaag caaccatagtacgcgccctgtagcggcgcattaagcgcggcgggtgtgg tggttacgcgcagcgtgaccgctacacttgccagcgccctagcgcccgc tcctttcgctttcttcccttcctttctcgccacgttcgccggctttccc cgtcaagctctaaatcggggggctccctttagggttccgatttagtgctt tacggcacctcgaccccaaaaaacttgattagggtgatggttcacgtag tgggccatcgccctgatagacggttttcgccctttgacgttggagtcc acgttctttaatagtggactcttgttccaaactggaacaacactcaacc ctatctcggtctattcttttgatttataagggattttgccgatttcggc ctattggttaaaaaatgagctgatttaacaaaaatttaacgcgaatttt aacaaaatattaacgcttacaatttaaatatttgcttatacaatcttcc tgttttggggcttttctgattatcaaccggggtacatatgattgacat gctagttttacgattaccgttcatcgattctcttgtttgctccagactc tcaggcaatgacctgatagcctttgtagagacctctcaaaaatagctac cctctccggcatgaatttatcagctagaacggttgaatatcatattgat ggtgatttgactgtctccggcctttctcacccgtttgaatctttaccta cacattactcaggcattgcatttaaaatatatgagggttctaaaaattt ttatccttgcgttgaaataaaggcttctcccgcaaaagtattacagggt cataatgttttggtacaaccgatttagctttatgctctgaggctttat tgcttaattttgctaattctttgccttgcctgtatgatttattggatgt tggaatcgcctgatgcggtattttctccttacgcatctgtgcggtattt cacaccGCATATGGTGCactctcagtacaatctgctctgatgccgcata gttaagccagccccgacacccgccaacacccgctgacgcgccctgacgg gcttgtctgctcccggcatccgcttacagacaagctgtgaccgtctccg ggagctgcatgtgtcagaggttttcaccgtcatcaccgaaacgcgcgag acgaaagggcctcgtgatacgcctatttttataggttaatgtcatgata ataatggtttcttagacgtcaggtggcacttttcggggaaatgtgcgcg gaacccctatttgtttatttttctaaatacattcaaatatgtatccgct catgagacaataaccctgataaatgcttcaataatattgaaaaaggaag agtatgagccatattcaacgggaaacgtcttgctctaggccgcgattaa attccaacatggatgctgatttatatgggtataaatgggctcgcgataa tgtcgggcaatcaggtgcgacaatctatcgattgtatgggaagcccgat gcgccagagttgtttctgaaacatggcaaaggtagcgttgccaatgatg ttacagatgagatggtcagactaaactggctgacggaatttatgcctct tccgaccatcaagcattttatccgtactcctgatgatgcatggttactc accactgcgatccctgggaaaacagcattccaggtattagaagaatatc ctgattcaggtgaaaatattgttgatgcgctggcagtgttcctgcgccg gttgcattcgattcctgtttgtaattgtccttttaacagcgatcgcgta tttcgtctcgctcaggcgcaatcacgaatgaataacggtttggttgatg cgagtgattttgatgacgagcgtaatggctggcctgttgaacaagtctg gaaagaaatgcataaacttttgccattctcaccggattcagtcgtcact catggtgatttctcacttgataaccttattttttgacgaggggaaattaa taggttgtattgatgttggacgagtcggaatcgcagaccgataccagga tcttgccatcctatggaactgcctcggtgagttttctccttcattacag aaacggcttttttcaaaaatatggtattgataatcctgatatgaataaat tgcagtttcatttgatgctcgatgagttttctaactgtcagaccaagt ttactcatatatacttttagattgatttaaaacttcattttttaatttaaa aggatctaggtgaagatcctttttgataatctcatgaccaaaatccctt aacgtgagttttcgttccactgagcgtcagacccgtagaaaagatcaa aggatcttcttgagatcctttttttctgcgcgtaatctgctgcttgcaa acaaaaaaaccaccgctaccagcggtggtttgtttgccggatcaagagc taccaactctttttccgaaggtaactggcttcagcagagcgcagatacc aaatactgttcttctagtgtagccgtagttaggccaccacttcaagaac tctgtagcaccgcctacatacctcgctctgctaatcctgttacCAGTGG CTGctgccagtggcgataagtcgtgtcttaccgggttggactcaagacg atagttaccggataaggcgcagcggtcgggctgaacggggggttcgtgc acacagcccagcttggagcgaacgacctacaccgaactgagatacctac agcgtgagctatgagaaagcgccacgcttcccgaagggagaaaggcgga caggtatccggtaagcggcagggtcggaacaggagagcgcacgagggag cttccaggggaaacgcctggtatctttatagtcctgtcgggtttcgcc acctctgacttgagcgtcgatttttgtgatgctcgtcaggggggcggag cctatggaaaaacgccagcaacgcggcctttttacggttcctggcctt tgctggccttttgctcacatgttctttcctgcgttatcccctgattctg tggataaccgtattaccgcctttgagtgagctgataccgctcgccgcag ccgaacgaccgagcgcagcgagtcagtgagcgaggaagcggaagagcgc ccaatacgcaaaccgcctctccccgcgcgttggccgattcattaatgca gc Origin of Replication Sequence In some aspects, an origin of replication sequence can comprise, consist essentially of, or consist of any origin of replication sequence known in the art. The origin of replication sequence can be a bacterial origin of replication sequence, thereby allowing the rAAV vector comprising said bacterial origin of replication sequence to be produced, propagated and maintained in bacteria, using methods standard in the art.

In some aspects, an origin of replication sequence can comprise, consist essentially of, or consist of a pUC19 or M13 origin of replication sequence. A pUC19 origin of replication sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:12 or 15.

Antibiotic Resistance Genes

In some aspects, rAAV vectors and/or rAAV viral vectors of the disclosure can comprise an antibiotic resistance gene.

In some aspects, an antibiotic resistance gene can comprise, consist essentially of, or consist of any antibiotic resistance genes known in the art. Examples of antibiotic resistance genes known in the art include, but are not limited to kanamycin resistance genes, spectinomycin resistance genes, streptomycin resistance genes, ampicillin resistance genes, carbenicillin resistance genes, bleomycin resistance genes, erythromycin resistance genes, polymyxin B resistance genes, tetracycline resistance genes and chloramphenicol resistance genes.

In some aspects, an antibiotic resistance gene can comprise, consist essentially of, or consist of a kanamycin antibiotic resistance gene. A kanamycin antibiotic resistance gene can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO:14. In an embodiment an antibiotic resistance gene can be operably linked to a promoter (e.g., SEQ ID NO:13).

Alternative rAAV Vectors and rAAV Viral Vectors Embodiments

The present disclosure provides the following embodiments:

1. An rAAV vector, comprising, in the 5' to 3' direction
   a) a first AAV ITR sequence;
   b) a promoter sequence;
   c) a transgene nucleic acid molecule, wherein the transgene nucleic acid molecule comprises a nucleic acid sequence encoding for a CSTB polypeptide;
   d) a polyA sequence; and
   e) a second AAV ITR sequence.

2. The rAAV vector of embodiment 1, wherein the nucleic acid molecule encoding for a CSTB polypeptide is a codon optimized nucleic acid molecule.

3. The rAAV vector of embodiment 1 or embodiment 2, wherein the CSTB polypeptide is encoded by the nucleic acid sequence of SEQ ID NO:9.

4. The rAAV vector of any one of the preceding embodiments, wherein the codon optimized transgene sequence eliminates a predicted donor splice site.

5. The rAAV vector of any one of the preceding embodiments, wherein the codon optimized transgene sequence has a higher GC content than the wild-type transgene sequence.

6. The rAAV vector of any one of the preceding embodiments, wherein the GC content of the codon optimized transgene sequence is more evenly distributed across the entire nucleic acid sequence as compared to the wild-type transgene sequence.

7. The rAAV vector of any one of the preceding embodiments, wherein the first AAV ITR sequence is a modified AAV2 ITR sequence.

8. The rAAV vector of embodiment 7, wherein the modified AAV2 ITR sequence comprises the nucleic acid sequence of SEQ ID NO:11.

9. The rAAV vector of any one of the preceding embodiments, wherein the second AAV ITR sequence is an AAV2 ITR sequence.

10. The rAAV vector of embodiment 9, wherein the AAV2 ITR sequence comprises the nucleic acid sequence of SEQ ID NO:2.

11. The rAAV vector of any one of the preceding embodiments, wherein the first AAV ITR sequence is a AAV2 ITR sequence.

12. The rAAV vector of embodiment 11, wherein the AAV2 ITR sequence comprises the nucleic acid sequence of SEQ ID NO:2.

13. The rAAV vector of any one of the preceding embodiments, wherein the second AAV ITR sequence is a modified AAV2 ITR sequence.

14. The rAAV vector of embodiment 13, wherein the modified AAV2 ITR sequence comprises the nucleic acid sequence of SEQ ID NO:11.

15. The rAAV vector of any one of the preceding embodiments, wherein the promoter sequence comprises a CBh promoter sequence.

16. The rAAV vector of embodiment 15, wherein the CBh promoter sequence comprises the nucleic acid sequence of SEQ ID NO:3.

17. The rAAV vector of any one of the preceding embodiments, wherein the promoter sequence comprises a CBA promoter sequence.

18. The rAAV vector of embodiment 17, wherein the CBA promoter sequence comprises the nucleic acid sequence of SEQ ID NO:5.

19. The rAAV vector of any one of the preceding embodiments, wherein the promoter sequence comprises a CMV enhancer sequence.

20. The rAAV vector of any embodiment 19, wherein the CMV enhancer sequence comprises the nucleic acid sequence of SEQ ID NO:4.

20A. The rAAV vector of any one of the preceding embodiments, wherein a hybrid intron is used to increase transgene expression, e.g., SEQ ID NO:6.

21. The rAAV vector of any one of the preceding embodiments, wherein the promoter sequence comprises a CBA intron sequence.

22. The rAAV vector of embodiment 21, wherein the CBA intron sequence comprises the nucleic acid sequence of SEQ ID NO:7.

23. The rAAV vector of any one of the preceding embodiments, wherein the promoter sequence comprises a MVM intron sequence.

24. The rAAV vector of embodiment 23, wherein the MVM intron sequence comprises the nucleic acid sequence of SEQ ID NO:8.

25. The rAAV vector of any one of the preceding embodiments, wherein the polyA sequence comprises a bGHpA sequence.

26. The rAAV vector of embodiment 25, wherein the bGHpA sequence comprises the nucleic acid sequence of SEQ ID NO:10.

27. An rAAV vector of any one of the preceding embodiments, comprising, in the 5' to 3' direction
   a) a first AAV ITR sequence comprising the nucleic acid sequence of SEQ ID NO:2;
   b) a promoter sequence comprising the nucleic acid sequence of SEQ ID NO:3;
   c) a transgene nucleic acid molecule encoding a CSTB polypeptide comprising SEQ ID NO:9;
   d) a polyA sequence comprising the nucleic acid sequence of SEQ ID NO:10; and e) a second AAV ITR sequence comprising the nucleic acid sequence of SEQ ID NO:11.

28. An rAAV vector of any one of the preceding embodiments, comprising, in the 5' to 3' direction
   a) a first AAV ITR sequence comprising the nucleic acid sequence of SEQ ID NO: 2;
   b) a promoter sequence comprising the nucleic acid sequence of SEQ ID NO:3;
   c) a transgene nucleic acid molecule encoding a CSTB polypeptide comprising SEQ ID NO:9;
   d) a polyA sequence comprising the nucleic acid sequence of SEQ ID NO:10; and
   e) a second AAV ITR sequence comprising the nucleic acid sequence of SEQ ID NO:11.

29. An rAAV viral vector comprising:
   a) an rAAV vector of any one of the preceding embodiments; and
   b) an AAV capsid protein.

30. The rAAV viral vector of embodiment 29, wherein the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

31. The rAAV viral vector of embodiment 30, wherein the AAV capsid protein is an AAV1 capsid protein.

32. The rAAV viral vector of embodiment 30, wherein the AAV capsid protein is an AAV2 capsid protein.

33. The rAAV viral vector of embodiment 30, wherein the AAV capsid protein is an AAV3 capsid protein.

34. The rAAV viral vector of embodiment 30, wherein the AAV capsid protein is an AAV4 capsid protein.

35. The rAAV viral vector of embodiment 30, wherein the AAV capsid protein is an AAV5 capsid protein.

36. The rAAV viral vector of embodiment 30, wherein the AAV capsid protein is an AAV6 capsid protein.

37. The rAAV viral vector of embodiment 30, wherein the AAV capsid protein is an AAV7 capsid protein.

38. The rAAV viral vector of embodiment 30, wherein the AAV capsid protein is an AAV8 capsid protein.

39. The rAAV viral vector of embodiment 30, wherein the AAV capsid protein is an AAV9 capsid protein.

40. The rAAV viral vector of embodiment 30, wherein the AAV capsid protein is an AAV10 capsid protein.

41. The rAAV viral vector of embodiment 30, wherein the AAV capsid protein is an AAV11 capsid protein.

42. The rAAV viral vector of embodiment 30, wherein the AAV capsid protein is an AAV12 capsid protein.

43. The rAAV viral vector of embodiment 30, wherein the AAV capsid protein is an AAV13 capsid protein.

44. The rAAV viral vector of embodiment 30, wherein the AAV capsid protein is an AAVPHP.B capsid protein.

45. The rAAV viral vector of embodiment 30, wherein the AAV capsid protein is an AAVrh74 capsid protein.

46. The rAAV viral vector of embodiment 60, wherein the AAV capsid protein is an AAVrh.10 capsid protein.

Compositions and Pharmaceutical Compositions

Provided herein are compositions comprising any of the isolated polynucleotides, rAAV vectors, and/or rAAV viral vectors described herein. In some aspects, the compositions can be pharmaceutical compositions. Accordingly, the present disclosure provides pharmaceutical compositions comprising any of the isolated polynucleotides, rAAV vectors, and/or rAAV viral vectors described herein.

The pharmaceutical composition, as described herein, can be formulated by any methods known or developed in the art of pharmacology, which include but are not limited to contacting the active ingredients (e.g., viral particles or recombinant vectors) with an excipient and/or additive and/or other accessory ingredient, dividing or packaging the product to a dose unit. The viral particles of this disclosure can be formulated with desirable features, e.g., increased stability, increased cell transfection, sustained or delayed release, biodistributions or tropisms, modulated or enhanced translation of encoded protein in vivo, and the release profile of encoded protein in vivo.

As such, the pharmaceutical composition can further comprise saline, lipidoids, liposomes, lipid nanoparticles, polymers, lipoplexes, core-shell nanoparticles, peptides, proteins, cells transfected with viral vectors (e.g., for transplantation into a subject), nanoparticle mimics or combinations thereof. In some aspects, the pharmaceutical composition is formulated as a nanoparticle. In some aspects, the nanoparticle is a self-assembled nucleic acid nanoparticle.

A pharmaceutical composition can be prepared, packaged, and/or sold in bulk, as a single unit dose, and/or as a plurality of single unit doses. The amount of the active ingredient is generally equal to the dosage of the active ingredient which would be administered to a subject and/or a convenient fraction of such a dosage such as, for example, one-half or one-third of such a dosage. The formulations can include one or more excipients and/or additives, each in an amount that together increases the stability of the viral vector, increases cell transfection or transduction by the viral vector, increases the expression of viral vector encoded protein, and/or alters the release profile of viral vector encoded proteins. In some aspects, the pharmaceutical composition comprises an excipient and/or additive. Non limiting examples of excipients and/or additives include solvents, dispersion media, diluents, or other liquid vehicles, dispersion or suspension aids, surface active agents, isotonic agents, thickening or emulsifying agents, preservatives, or combination thereof.

In some aspects, the pharmaceutical composition comprises a cryoprotectant. The term "cryoprotectant" refers to an agent capable of reducing or eliminating damage to a substance during freezing. Non-limiting examples of cryoprotectants include sucrose, trehalose, lactose, glycerol, dextrose, raffinose and/or mannitol.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

In some aspects, a pharmaceutical composition can comprise phosphate-buffered saline, D-sorbitol, sodium chloride, pluronic F-68 or any combination thereof.

In some aspects, a pharmaceutical composition can comprise sodium chloride, wherein the sodium chloride is present at a concentration of about 100 mM to about 500 mM, or about 200 mM to about 400 mM, or about 300 mM to about 400 mM. In some aspects, the sodium chloride can be present at a concentration of about 350 mM.

In some aspects, a pharmaceutical composition can comprise D-sorbitol, wherein the D-sorbitol is present at a concentration of about 1% to about 10%, or about 2.5% to about 7.5%. In some aspects, the D-sorbitol can be present at a concentration of about 5%.

In some aspects, a pharmaceutical composition can comprise pluronic F-68, wherein the pluronic F-68 is present at a concentration of about 0.00001% to about 0.01%, or about 0.0005% to about 0.005%. In some aspects, the pluronic F-68 can be present at a concentration of about 0.001%.

A pharmaceutical composition can comprise an rAAV vector and/or rAAV viral vector in a phosphate-buffered saline solution comprising sodium chloride at a concentration of 350 mM, D-sorbitol at a concentration of 5% and pluronic F-68 at a concentration of 0.001%.

A pharmaceutical composition can comprise an rAAV vector and/or rAAV viral vector comprising sodium chloride at a concentration of 350 mM, D-sorbitol at a concentration of 5% and pluronic F-68 at a concentration of 0.001%.

A pharmaceutical composition can comprise an rAAV vector and/or rAAV viral vector of in a phosphate-buffered saline solution comprising sodium chloride at a concentration of 350 mM, D-sorbitol at a concentration of 5%.

A pharmaceutical composition can comprise an rAAV vector and/or rAAV viral vector, wherein the pharmaceutical composition further comprises sodium chloride at a concentration of 350 mM, D-sorbitol at a concentration of 5%.

Methods of Using Compositions

The present disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal.

This disclosure provides methods of preventing or treating a disorder, comprising, consisting essentially of, or consisting of administering to a subject a therapeutically effective amount of any one of the rAAV vectors, rAAV viral vectors, compositions and/or pharmaceutical compositions disclosed herein.

In some aspects, the disease can be a genetic disorder involving a CSTB gene. As would be appreciated by the skilled artisan, such genetic disorders can cause one or more neurological symptoms in a subject, including, but not limited to, seizures, epilepsy, intellectual disability, schizophrenia, autism spectrum disorder (ASD), movement disorders, ataxia, tremors, behavior disorders, aggression, and/or hyperactivity, In some aspects, the epilepsy can be epilepsy with myoclonic-atonic seizures, genetic generalized epilepsy, non-acquired focal epilepsy, or any other epilepsy known in the art.

In some aspects, the seizures can be atypical absence seizures, atonic seizures, myoclonic seizures, or any other type of seizure known in the art.

In some aspects, a genetic disorder involving CSTB can be Unverricht-Lundborg disease (ULD).

In some aspects, a disease can be a disease that is characterized by the loss-of-function of at least one copy of the CSTB gene in the genome of a subject. In some aspects, a disease can be a disease that is characterized by a decrease in function of at least one copy of the CSTB gene in the genome of a subject. In some aspects, a disease can be a disease that is characterized by at least one mutation in at least one mutation in at least one copy of the CSTB gene in the genome of the subject.

A mutation in a CSTB gene can be any type of mutation that is known in the art. Non-limiting examples of mutations include somatic mutations, single nucleotide variants (SNVs), nonsense mutations, insertions, deletions, duplications, frameshift mutations, repeat expansions, short insertions and deletions (INDELs), long INDELs, alternative splicing, the products of alternative splicing, altered initiation of translation, the products of altered initiation of translation, proteomic cleavage, the products of proteomic cleavage.

In some aspects, a disease can be a disease that is characterized by a decrease in expression of the CSTB gene in a subject as compared to a control subject that does not have the disease. In some aspects, the decrease in expression can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the amount of CSTB in a subject as compared to a control subject that does not have the disease. In some aspects, the decrease in the amount of CSTB can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the activity of CSTB in a subject as compared to a control subject that does not have the disease. In some aspects, the decrease in the activity of CSTB can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in reuptake of the GABA neurotransmitter from the synaptic cleft as compared to a control subject that does not have the disease. In some aspects, the decrease in reuptake can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

A subject to be treated using the methods, compositions, pharmaceutical compositions, rAAV vectors or rAAV viral vectors of the present disclosure can have any of the diseases and/or symptoms described herein.

In some aspects, a subject can be less than 0.5 years of age, or less than 1 year of age, or less than 1.5 years of age, or less than 2 years of age, or at less than 2.5 years of age, or less than 3 years of age, or less than 3.5 years of age, or less than 3.5 years of age, or less than 4 years of age, or less than 4.5 years of age, or less than 5 years of age, or less than 5.5 years of age, or less than 6 years of age, or less than 6.5 years of age, or less than 7 years of age, or less than 7.5 years of age, or less than 8 years of age, or less than 8.5 years of age, or less than 9 years of age, or less than 9.5 years of age, or less than 10 years of age. In some aspects the subject can be less than 11 years of age, less than 12 years of age, less than 13 years of age, less than 14 years of age, less than 15 years of age, less than 20 years of age, less than 30 years of age, less than 40 years of age, less than 50 years of age, less than 60 years of age, less than 70 years of age, less than 80 years of age, less than 90 years of age, less than 100 years of age, less than 110 years of age, or less than 120 years of age. In some aspects, a subject can be less than 0.5 years of age. In some aspects, a subject can be less than 4 years of age. In some aspects, a subject can be less than 10 years of age.

The methods of treatment and prevention disclosed herein can be combined with appropriate diagnostic techniques to identify and select patients for the therapy or prevention.

The disclosure provides methods of increasing the level of a protein (e.g., CSTB) in a host cell, comprising contacting the host cell with any one of the rAAV viral vectors disclosed herein, comprising a transgene nucleic acid molecule encoding the protein. In some aspects, the protein is a therapeutic protein. In some aspects, the host cell is in vitro, in vivo, or ex vivo. In some aspects, the host cell is derived from a subject. In some aspects, the subject suffers from a disorder, which results in a reduced level and/or functionality of the protein, as compared to the level and/or functionality of the protein in a normal subject.

In some aspects, the level of the protein is increased to level of about $1\times10^{-7}$ ng, about $3\times10^{-7}$ ng, about $5\times10^{-7}$ ng, about $7\times10^{-7}$ ng, about $9\times10^{-7}$ ng, about $1\times10^{-6}$ ng, about $2\times10^{-6}$ ng, about $3\times10^{-6}$ ng, about $4\times10^{-6}$ ng, about $6\times10^{-6}$ ng, about $7\times10^{-6}$ ng, about $8\times10^{-6}$ ng, about $9\times10^{-6}$ ng, about $10\times10^{-6}$ ng, about $12\times10^{-6}$ ng, about $14\times10^{-6}$ ng, about $16\times10^{-6}$ ng, about $18\times10^{-6}$ ng, about $20\times10^{-6}$ ng, about $25\times10^{-6}$ ng, about $30\times10^{-6}$ ng, about $35\times10^{-6}$ ng, about $40\times10^{-6}$ ng, about $45\times10^{-6}$ ng, about $50\times10^{-6}$ ng, about $55\times10^{-6}$ ng, about $60\times10^{-6}$ ng, about $65\times10^{-6}$ ng, about $70\times10^{-6}$ ng, about $75\times10^{-6}$ ng, about $80\times10^{-6}$ ng, about $85\times10^{-6}$ ng, about $90\times10^{-6}$ ng, about $95\times10^{-6}$ ng, about $10\times10^{-5}$ ng, about $20\times10^{-5}$ ng, about $30\times10^{-5}$ ng, about $40\times10^{-5}$ ng, about $50\times10^{-5}$ ng, about $60\times10^{-5}$ ng, about $70\times10^{-5}$ ng, about $80\times10^{-5}$ ng, or about $90\times10^{-5}$ ng in the host cell.

The disclosure provides methods of introducing a gene of interest (e.g., CSTB) to a cell in a subject comprising contacting the cell with an effective amount of any one of the rAAV viral vectors disclosed herein, wherein the rAAV viral vectors contain any one of the rAAV vectors disclosed herein, comprising the gene of interest.

In some aspects of the methods of the present disclosure, a subject can also be administered a prophylactic immunosuppressant treatment regimen in addition to being administered an rAAV vector or rAAV viral vector of the present disclosure. In some aspects, an immunosuppressant treatment regimen can comprise administering at least one immunosuppressive therapeutic. Non limiting examples of immunosuppressive therapeutics include, but are not limited to, Sirolimus (rapamycin), acetaminophen, diphenhydramine, IV methylprednisolone, prednisone, or any combination thereof. An immunosuppressive therapeutic can be administered prior to the day of administration of the rAAV vector and/or rAAV viral vector, on the same day as the administration of the rAAV vector and/or rAAV viral vector, or any day following the administration of the rAAV vector and/or rAAV viral vector.

A "subject" of diagnosis or treatment is a cell or an animal such as a mammal, or a human. A subject is not limited to a specific species and includes non-human animals subject to diagnosis or treatment and those subject to infections or animal models, including, without limitation, simian, murine, rat, canine, feline, equine, or leopard species, as well as other livestock, sport animals, or pets. In some aspects, the subject is a human.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein the term "effective amount" intends to mean a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of gene therapy, the effective amount can be the amount sufficient to result in regaining part or full function of a gene that is deficient in a subject. In some aspects, the effective amount of an rAAV viral vector is the amount sufficient to result in expression of a gene in a subject such that CSTB is produced. The skilled artisan will be able to determine appropriate amounts depending on these and other factors.

In some aspects, the effective amount will depend on the size and nature of the application in question. It will also depend on the nature and sensitivity of the target subject and the methods in use. The skilled artisan will be able to determine the effective amount based on these and other considerations. The effective amount can comprise, consist essentially of, or consist of one or more administrations of a composition depending on the embodiment.

As used herein, the term "administer" or "administration" intends to mean delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and other animals, treating veterinarian.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage can be impacted by the route of administration. Suitable dosage formulations and methods of administering the agents are known in the art. Non-limiting examples of such suitable dosages can be as low as $10^9$ vector genomes to as much as $10^{17}$ vector genomes per administration.

In some aspects of the methods described herein, the number of viral particles (e.g., rAAV viral vectors) administered to the subject ranges from about $10^9$ to about $10^{17}$. In some aspects, about $10^{10}$ to about $10^{12}$, about $10^{11}$ to about $10^{13}$, about $10^{11}$ to about $10^{12}$, about $10^{11}$ to about $10^{14}$, about $10^{12}$ to about $10^{16}$, about $10^{13}$ to about $10^{16}$, about $10^{11}$ to about $10^{18}$, about $10^{14}$ to about $10^{15}$, about $5\times10^{11}$ to about $5\times10^{12}$, or about $10^{12}$ to about $10^{13}$ viral particles are administered to the subject.

In some aspects of the methods described herein, the number of viral particles (e.g., rAAV viral vectors) administered to the subject is at least about $10^{10}$, or at least about $10^{11}$, or at least about $10^{12}$, or at least about $10^{13}$, or at least about $10^{14}$, or at least about $10^{15}$, or at least about $10^{16}$, or at least about $10^{17}$ viral particles.

In some aspects of the methods described herein, the number of viral particles (e.g., rAAV viral vectors) administered to the subject can depend on the age of the subject. In non-limiting examples, a subject that is 7 years of age or older can be administered about $10\times10^{14}$ viral particles, a subject that is about 4 years of age to about 7 years of age can be administered about $10\times10^{14}$ viral particles, a subject that is about 3 years of age to about 4 years of age can be administered about $9\times10^{14}$ viral particles, a subject that is about 2 years of age to about 3 years of age can be about $8.2\times10^{14}$ viral particles, a subject that is about 1 year of age to about 2 years of age can be administered about $7.3\times10^{14}$ viral particles, a subject that is about 0.5 years of age to about 1 year of age can be administered about $4\times10^{14}$ viral particles, or a subject that is less than 0.5 years of age can be administered $3\times10^{14}$ viral particles.

In some aspects, the amounts of viral particles in a composition, pharmaceutical composition, or the amount of viral particles administered to a patient can calculated based on the percentage of viral particles that are predicted to contain viral genomes.

In some aspects, rAAV viral vectors of the present disclosure can be introduced to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally; such introduction can also be intra-arterial, intracardiac, subventricular, epidural, intracerebral, intracerebroventricular, sub-retinal, intravitreal, intraarticular, intraperitoneal, intrauterine, intra-nerve or any combination thereof. In some aspects, the viral particles are delivered to a desired target tissue, e.g., to the lung, eye, or CNS, as non-limiting examples. In some aspects, delivery of viral particles is systemic. The intracisternal route of administration involves administration of a drug directly into the cerebrospinal fluid of the brain ventricles. It could be performed by direct injection into the cisterna magna or via a permanently positioned tube. In some aspects, the rAAV viral vectors of the present disclosure are administered intrathecally.

In some aspects, the rAAV viral vectors of the present disclosure repair a gene deficiency in a subject. In some aspects, the ratio of repaired target polynucleotide or polypeptide to unrepaired target polynucleotide or polypeptide in a successfully treated cell, tissue, organ or subject is at least about 1.5:1, about 2:1, about 3:1, about 4:1, about 5:1, about 6:1, about 7:1, about 8:1, about 9:1, about 10:1, about 20:1, about 50:1, about 100:1, about 1000:1, about 10,000:1, about 100,000:1, or about 1,000,000:1. The amount or ratio of repaired target polynucleotide or polypeptide can be determined by any method known in the art, including but not limited to western blot, northern blot, Southern blot, PCR, sequencing, mass spectrometry, flow cytometry, immunohistochemistry, immunofluorescence, fluorescence in situ hybridization, next generation sequencing, immunoblot, and ELISA.

Administration of the rAAV vectors, rAAV viral vectors, compositions or pharmaceutical compositions of this disclosure can be effected in one dose, continuously or intermittently throughout the course of treatment. In some aspects, the rAAV vectors, rAAV viral vectors, compositions, or pharmaceutical compositions of this disclosure are parenterally administered by injection, infusion, or implantation.

In some aspects, the rAAV viral vectors of this disclosure show enhanced tropism for brain and cervical spine. In some aspects, the rAAV viral vectors of the disclosure can cross the blood-brain-barrier (BBB).

Methods of Manufacture

A variety of approaches can be used to produce rAAV viral vectors of the present disclosure. In some aspects, packaging is achieved by using a helper virus or helper plasmid and a cell line. The helper virus or helper plasmid contains elements and sequences that facilitate viral vector production. In another aspect, the helper plasmid is stably incorporated into the genome of a packaging cell line, such that the packaging cell line does not require additional transfection with a helper plasmid.

In some aspects, the cell is a packaging or helper cell line. In some aspects, the helper cell line is eukaryotic cell; for example, an HEK 293 cell or 293T cell. In some aspects, the helper cell is a yeast cell or an insect cell.

In some aspects, the cell comprises a nucleic acid encoding a tetracycline activator protein; and a promoter that regulates expression of the tetracycline activator protein. In some aspects, the promoter that regulates expression of the tetracycline activator protein is a constitutive promoter. In some aspects, the promoter is a phosphoglycerate kinase promoter (PGK) or a CMV promoter.

A helper plasmid can comprise, for example, at least one viral helper DNA sequence derived from a replication-incompetent viral genome encoding in trans all virion proteins required to package a replication incompetent AAV, and for producing virion proteins capable of packaging the replication-incompetent AAV at high titer, without the production of replication competent AAV.

Helper plasmids for packaging AAV are known in the art, see, e.g., U.S. Patent Pub. No. 2004/0235174 A1, incorporated herein by reference. As stated therein, an AAV helper plasmid can contain as helper virus DNA sequences, by way of non-limiting example, the Ad5 genes E2A, E4 and VA, controlled by their respective original promoters or by heterologous promoters. AAV helper plasmids can additionally contain an expression cassette for the expression of a marker protein such as a fluorescent protein to permit the simple detection of transfection of a desired target cell.

The disclosure provides methods of producing rAAV viral vectors comprising transfecting a packaging cell line with any one of the AAV helper plasmids disclosed herein; and any one of the rAAV vectors disclosed herein. In some aspects, the AAV helper plasmid and rAAV vector are co-transfected into the packaging cell line. In some aspects, the cell line is a mammalian cell line, for example, human embryonic kidney (HEK) 293 cell line. The disclosure provides cells comprising any one of the rAAV vectors and/or rAAV viral vectors disclosed herein.

As used herein, the term "helper" in reference to a virus or plasmid refers to a virus or plasmid used to provide the additional components necessary for replication and packaging of any one of the rAAV vectors disclosed herein. The components encoded by a helper virus can include any genes required for virion assembly, encapsidation, genome replication, and/or packaging. For example, the helper virus or plasmid can encode necessary enzymes for the replication of the viral genome. Non-limiting examples of helper viruses and plasmids suitable for use with AAV constructs include pHELP (plasmid), adenovirus (virus), or herpesvirus (virus). In some aspects, the pHELP plasmid can be the pHELPK plasmid, wherein the ampicillin expression cassette is exchanged with a kanamycin expression cassette.

As used herein, a packaging cell (or a helper cell) is a cell used to produce viral vectors. Producing recombinant AAV viral vectors requires Rep and Cap proteins provided in trans as well as gene sequences from Adenovirus that help AAV replicate. In some aspects, Packaging/helper cells contain a plasmid is stably incorporated into the genome of the cell. In other aspects, the packaging cell can be transiently transfected. Typically, a packaging cell is a eukaryotic cell, such as a mammalian cell or an insect cell.

Kits

The isolated polynucleotides, expression cassettes, rAAV vectors, rAAV viral vectors, compositions, and/or pharmaceutical compositions described herein can be assembled into pharmaceutical or diagnostic or research kits to facilitate their use in therapeutic, diagnostic, or research applications. In some aspects, the kits of the present disclosure include any one of the isolated polynucleotides, expression cassettes, rAAV vectors, rAAV viral vectors, compositions, pharmaceutical compositions, host cells, isolated tissues, as described herein.

In some aspects, a kit further comprises instructions for use. Specifically, such kits can include one or more agents described herein, along with instructions describing the intended application and the proper use of these agents. In some aspects, the kit can include instructions for mixing one or more components of the kit and/or isolating and mixing a sample and applying to a subject. In some aspects, agents in a kit are in a pharmaceutical formulation and dosage suitable for a particular application and for a method of administration of the agents. Kits for research purposes can contain the components in appropriate concentrations or quantities for running various experiments.

The kit can be designed to facilitate use of the methods described herein and can take many forms. Each of the compositions of the kit, where applicable, can be provided in liquid form (e.g., in solution), or in solid form, (e.g., a dry powder). In certain cases, some of the compositions can be constitutable or otherwise processable (e.g., to an active form), for example, by the addition of a suitable solvent or other species (for example, water or a cell culture medium), which may or may not be provided with the kit. In some aspects, the compositions can be provided in a preservation solution (e.g., cryopreservation solution). Nonlimiting examples of preservation solutions include DMSO, paraformaldehyde, and CryoStor® (Stem Cell Technologies, Vancouver, Canada). In some aspects, the preservation solution contains an amount of metalloprotease inhibitors.

In some aspects, the kit contains any one or more of the components described herein in one or more containers. Thus, in some aspects, the kit can include a container housing agents described herein. The agents can be in the form of a liquid, gel or solid (powder). The agents can be prepared sterilely, packaged in a syringe and shipped refrigerated. Alternatively, they can be housed in a vial or other container for storage. A second container can have other agents prepared sterilely. Alternatively, the kit can include the active agents premixed and shipped in a syringe, vial, tube, or other container. The kit can have one or more or all of the components required to administer the agents to a subject, such as a syringe, topical application devices, or IV needle tubing and bag.

Administration to a subject can be by any route, including intraduodenally, parenterally (including intravenous, subcutaneous, intramuscular, intravascular or by infusion), intrathecally, or systemically.

Expression cassettes and vectors can be delivered by any suitable method. Exemplary methods include intracranial injection, stereotaxic injection, and intravenous injection. In some embodiments, nucleic acid expression cassettes are delivered as viral vectors.

Further Definitions

Unless the context indicates otherwise, it is specifically intended that the various features described herein can be used in any combination. Moreover, the disclosure also contemplates that, in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Any single term, single element, single phrase, group of terms, group of phrases, or group of elements described herein can each be specifically excluded from the claims.

Unless explicitly indicated otherwise, all specified aspects, embodiments, features, and terms intend to include both the recited aspect, embodiment, feature, or term and biological equivalents thereof.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (RI. Freshney, ed. (1987)).

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps and those that do not materially affect the basic and novel characteristic(s) of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure. In each instance herein any of the terms "comprising," "consisting essentially of," and "consisting of" can be replaced with either of the other two terms, while retaining their ordinary meanings.

All numerical designations, e.g., pH, temperature, time, concentration, and molecular weight, including ranges, are approximations which are varied (+) or (−) by increments of 1.0 or 0.1, as appropriate, or, alternatively, by a variation of +/−15%, 10%, 5%, 2%. It is to be understood, although not always explicitly stated, that all numerical designations are preceded by the term "about". It also is to be understood, although not always explicitly stated, that the reagents described herein are merely exemplary and that equivalents of such are known in the art. The term "about," as used herein when referring to a measurable value such as an amount or concentration and the like, is meant to encompass variations of 20%, 10%, 5%, 1%, 0.5%, or even 0.1% of the specified amount.

The terms "acceptable," "effective," or "sufficient" when used to describe the selection of any components, ranges, dose forms, etc. disclosed herein intend that said component, range, dose form, etc. is suitable for the disclosed purpose.

Also, as used herein, "and/or" refers to and encompasses any and all possible combinations of one or more of the associated listed items, as well as the lack of combinations when interpreted in the alternative ("or").

Unless specifically recited, the term "host cell" includes a eukaryotic host cell, including, for example, fungal cells, yeast cells, higher plant cells, insect cells and mammalian cells. Non-limiting examples of eukaryotic host cells include simian, bovine, porcine, murine, rat, avian, reptilian and human, e.g., HEK293 cells and 293T cells.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi stranded DNA or RNA, genomic DNA, cDNA, DNA-RNA hybrids, or a polymer comprising, consisting essentially of, or consisting of purine and pyrimidine bases or other natural, chemically or biochemically modified, non-natural, or derivatized nucleotide bases.

A "gene" refers to a polynucleotide containing at least one open reading frame (ORF) that is capable of encoding a particular polypeptide or protein. A "gene product" or, alternatively, a "gene expression product" refers to the amino acid sequence (e.g., peptide or polypeptide) generated when a gene is transcribed and translated.

As used herein, "expression" refers to the two-step process by which polynucleotides are transcribed into mRNA and/or the process by which the transcribed mRNA is subsequently translated into peptides, polypeptides, or proteins. If the polynucleotide is derived from genomic DNA, expression can include splicing of the mRNA in a eukaryotic cell.

"Under transcriptional control" is a term well understood in the art and indicates that transcription of a polynucleotide sequence, usually a DNA sequence, depends on its being operably linked to an element that contributes to the initiation of, or promotes, transcription. "Operably linked" intends that the polynucleotides are arranged in a manner that allows them to function in a cell. In one aspect, promoters can be operably linked to the downstream sequences.

The term "encode" as it is applied to polynucleotides and/or nucleic acid sequences refers to a polynucleotide and/or nucleic acid sequence which is said to "encode" a polypeptide if, in its native state or when manipulated by methods well known to those skilled in the art, it can be transcribed to produce the mRNA for the polypeptide and/or a fragment thereof. The antisense strand is the complement of such a nucleic acid, and the encoding sequence can be deduced therefrom.

The term "protein", "peptide" and "polypeptide" are used interchangeably and in their broadest sense to refer to a compound of two or more subunits of amino acids, amino acid analogs or peptidomimetics. The subunits can be linked by peptide bonds. In another aspect, the subunit can be linked by other bonds, e.g., ester, ether, etc. A protein or peptide must contain at least two amino acids and no limitation is placed on the maximum number of amino acids which can comprise, consist essentially of, or consist of a protein's or peptide's sequence. As used herein the term "amino acid" refers to either natural and/or unnatural or synthetic amino acids, including glycine and both the D and L optical isomers, amino acid analogs and peptidomimetics.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In some aspects, the signal peptide is removed following localization. Examples of signal peptides are well known in the art. Non-limiting examples are those described in U.S. Pat. Nos. 8,853,381, 5,958,736, and 8,795,965. In some aspects, the signal peptide can be an IDUA signal peptide.

The terms "equivalent" or "biological equivalent" are used interchangeably when referring to a particular molecule, biological material, or cellular material and intend those having minimal homology while still maintaining desired structure or functionality. Non-limiting examples of equivalent polypeptides include a polypeptide having at least about 60%, at least about 65%, at least about 70%, at least about 75%, at least about 80%, at least about 85%, at least about 90%, at least about 95% identity or at least about 99% identity to a reference polypeptide (for instance, a wild-type polypeptide); or a polypeptide which is encoded by a polynucleotide having at least about 70%, at least about 75%, at least about 80%, at least about 85%, at least about 90%, at least about 95% identity, at least about 97% sequence identity or at least about 99% sequence identity to the reference polynucleotide (for instance, a wild-type polynucleotide).

"Homology" or "identity" or "similarity" refers to sequence similarity between two peptides or between two nucleic acid molecules. Percent identity can be determined by comparing a position in each sequence that can be aligned for purposes of comparison. When a position in the compared sequence is occupied by the same base or amino acid, then the molecules are identical at that position. A degree of identity between sequences is a function of the number of matching positions shared by the sequences. "Unrelated" or "non homologous" sequences share less than 40% identity, less than 25% identity, with one of the sequences of the present disclosure. Alignment and percent sequence identity can be determined for the nucleic acid or amino acid sequences provided herein by importing said nucleic acid or amino acid sequences into and using ClustalW (available at https://genome.jp/tools-bin/clustalw/). For example, the ClustalW parameters used for performing the protein sequence alignments found herein were generated using the Gonnet (for protein) weight matrix. In some aspects, the ClustalW parameters used for performing nucleic acid sequence alignments using the nucleic acid sequences found herein are generated using the ClustalW (for DNA) weight matrix.

As used herein, amino acid modifications can be amino acid substitutions, amino acid deletions or amino acid insertions. Amino acid substitutions can be conservative amino acid substitutions or non-conservative amino acid substitutions. A conservative replacement (also called a conservative mutation, a conservative substitution or a conservative variation) is an amino acid replacement in a protein that changes a given amino acid to a different amino acid with similar biochemical properties (e.g., charge, hydrophobicity or size). As used herein, "conservative variations" refer to the replacement of an amino acid residue by another, biologically similar residue. Examples of conservative variations include the substitution of one hydrophobic residue such as isoleucine, valine, leucine or methionine for another; or the substitution of one charged or polar residue for another, such as the substitution of arginine for lysine, glutamic acid for aspartic acid, glutamine for asparagine, and the like. Other illustrative examples of conservative substitutions include the changes of: alanine to serine; asparagine to glutamine or histidine; aspartate to glutamate; cysteine to serine; glycine to proline; histidine to asparagine or glutamine; lysine to arginine, glutamine, or glutamate; phenylalanine to tyrosine, serine to threonine; threonine to serine; tryptophan to tyrosine; tyrosine to tryptophan or phenylalanine; and the like.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide can be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is a DNA molecule that is typically separate from and capable of replicating independently of the chromosomal DNA. In many cases, it is circular and double-stranded. Plasmids provide a mechanism for horizontal gene transfer within a population of microbes and typically provide a selective advantage under a given environmental state. Plasmids can carry genes that provide resistance to naturally occurring antibiotics in a competitive environmental niche, or, alternatively, the proteins produced can act as toxins under similar circumstances. It is known in the art that while plasmid vectors often exist as extrachromosomal circular DNA molecules, plasmid vectors can also be designed to be stably integrated into a host chromosome either randomly or in a targeted manner, and such integration can be accomplished using either a circular plasmid or a plasmid that has been linearized prior to introduction into the host cell.

"Plasmids" used in genetic engineering are called "plasmid vectors". Many plasmids are commercially available for such uses. The gene to be replicated is inserted into copies of a plasmid containing genes that make cells resistant to particular antibiotics, and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria or eukaryotic cells containing a plasmid harboring the gene of interest, which can be induced to produce large amounts of proteins from the inserted gene.

In aspects where gene transfer is mediated by a DNA viral vector, such as an adenovirus (Ad) or adeno-associated virus (AAV), a vector construct refers to the polynucleotide comprising, consisting essentially of, or consisting of the viral genome or part thereof, and a transgene.

The term "tissue" is used herein to refer to tissue of a living or deceased organism or any tissue derived from or designed to mimic a living or deceased organism. The tissue can be healthy, diseased, and/or have genetic mutations. The biological tissue can include any single tissue (e.g., a collection of cells that can be interconnected), or a group of tissues making up an organ or part or region of the body of an organism. The tissue can comprise, consist essentially of, or consist of a homogeneous cellular material or it can be a composite structure such as that found in regions of the body including the thorax which for instance can include lung tissue, skeletal tissue, and/or muscle tissue. Exemplary tissues can include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

EXAMPLES

Example 1: Study Design and Material and Methods

It was hypothesized that replacing Cystatin B would improve the neuropathology and neurobehavioral phenotypes of Cstb-deficient mice. After designing the human codon-optimized CSTB plasmid and packaging in adeno-associated virus 9 (AAV9), the AAV-CSTB was administered at two different time-points (p21 and p60) by intrathecal (IT) injections. Based on injection and sacrifice timepoints, this study comprised of three different cohorts:

Cohort-1 injected at p21 and sacrificed at 2 months of age

Cohort-2 injected at p21 and sacrificed at 7-9 months of age

Cohort-3 injected at p60 and sacrificed at 7-9 months of age

Cohort-1 was sacrificed at 2 months of age to study the effect of treatment on early-onset neuropathological phenotypes including neuroinflammation and granular cell apoptosis. Cohorts 2 and 3 were sacrificed at age of 7 to 9 months to study the effect of treatment on the behavioral phenotype (ataxia) and late-onset neuroinflammation and neurodegeneration.

Plasmid Construction and Viral Packaging the CBh-hCSTB-bGHpA plasmid (FIG. 1) was designed and developed as containing the transgene of a human CSTB codon-optimized construct (hCSTB). The DNA sequence was modified (codon-optimized) such that the final amino acid sequence was unchanged but there is a significant increase in expression levels of the heterologous gene. The transgene comprises a human AGA DNA coding sequence of 297-bp between an 800-bp CBh promoter and a 250-bp bGHpA signal. The CBh promoter and bGHpA are utilized for their ability to drive strong expression. The final plasmid was packaged into a scAAV9 at the University of North Carolina (UNC) Vector Core facility. Self-complementary (sc) AAV vector which is more efficient at transduction compared to traditional single-stranded (ss) AAV vectors was used.

Mice

CSTB-deficient mouse model was described previously Pennacchio et al., 1998. Knock out and 129/SvJ WT mice, littermates born from heterozygous breeding pairs were used for all experiments. PCR for genotyping was performed as described by Pennacchio et al., 1998. Both sexes were used. $7\times10^{11}$ vector genomes or 5 µl PBS were injected. Mice were sacrificed by cervical dislocation, and brain harvested and cut into two hemispheres, one fixed in formalin for paraffin embedding and immunohistochemistry, the other snap-frozen in liquid nitrogen for biochemical analyses. All procedures were carried out according to NIH guidelines and the animal care committee regulations at the University of Texas Southwestern Medical Center.

CSTB Immunohistochemistry

Sections (5 µm) were mounted on glass slides, de-paraffinated and rehydrated by processing through xylenes and decreasing concentrations of ethanol in water and subjected to antigen retrieval using citrate buffer pH 6.0 (Sigma, C9999). Endogenous peroxidase activity was blocked for 10 min with BLOXALL solution (Vector labs, MP-7601). Sections were incubated with cystatin B (Santa Cruz) antibody diluted in normal horse serum overnight at 4° C., then successively incubated with Amplifier Antibody and ImmPRESS Polymer Reagent (Vector labs, MP-7601) and the ImmPACT DAB EqV working solution (Vector labs, MP-7601) until desired stain intensity.

Western Blot

Tissue lysate was made by homogenizing frozen ground mice brain using ice-cold RIPA lysis buffer (NaCl 150 mM, NP-40 1%, Sodium doxycholate 0.5%, SDS 0.1%, Tris HCl 50 mM pH 8.0) containing protease inhibitors (PMSF 1 mM, Leupetin 5 µg/mL, Pepstatin 10 µg/mL, Aprotinin 20 KIU/mL, NaF 50 mM). Lysates were centrifuged at 15,000 g for 5 min at 4° C. and supernatants were collected. Protein concentration was measured using Bradford assay reagent (ThermoScientific). A serial dilution of Albumin standard (ThermoScientific) was utilized to generate standard curve for protein quantification.

Equal amount of whole protein from each sample was subjected to SDS-PAGE electrophoresis TGX Stain-Free FastCast Acrylamide kit (BioRad). Protein bands were transferred to polyvinylidene difluoride (PVDF) membrane (Millipore) overnight at 4° C. Primary antibodies (1:1000 dilution) used in this study were against cystatin B (Santa Cruz). Protein calorimetry was performed using Image Lab software (BioRad). The intensity of each protein band was normalized to the intensity of its corresponding whole protein lane image.

Quantitative Real-Time PCR

Fresh frozen mouse brain tissue was ground using mortar and pestle. The ground tissue was subjected to total RNA extraction using TriZol (Invitrogen) and then RNA purification using PureLink RNA Mini Kit (Invitrogen) following manufacturer instruction. cDNA was generated using iScript Reverse Transcription SuperMix kit (BioRad). QuantStudio 7 Pro System thermo-cycler (ThermoFischer Scientific) and SYBR Green Master Mix (Bio-Rad) were utilized to perform Quantitative real-time PCR. Data are shown as fold change relative to control samples using the ΔΔCq method with Rpl4 as an internal control gene.

Total Brain Weight

Snap-frozen ground brain tissue was weighed, and the measurement was used as the final brain weight to compare total brain loss as a measurement of neurodegeneration.

TUNEL Staining and Quantitation

Terminal Deoxynucleotidyl Transferase-Mediated dUTP Nick-End Labeling (TUNEL) assay was used on cerebellar sections to compare cerebellar granule cell apoptosis respectively. The assay was performed according to the manufacturer's instructions for paraffin embedded tissues as described by [Houseweart et al., *J. Neurobiol.*, 56: 315-327 (2003) and Penacchio et al., *Nat Genet*, 20(3), 251-258 (1998)]. A total of two adjacent layers per paraffin embedded cerebellar hemisphere of each mouse were immunostained with TUNEL and the number of fluorescently labeled apoptotic cells were quantitated using quantified using ImageJ and iLastik (v. 1.3.3) image analysis software.

Rotarod Analysis

Starting from six-month-old, $Cstb^{-/-}$ mice show mild signs of ataxia when challenged to walk on uneven surfaces and significantly lose their ability to remain on both the still and rotating rotarod as they age. 7-9-month-old mice (n=9-11) of each group were tested for ataxia by using a rotating-rod apparatus as described by Pennacchio et al., 1998. The rotating-rod testing was applied at both 0 and 2 rpm speeds and the time between their initial placement on the rod and a fall was recorded. Briefly, after 2 trial runs, mouse was placed on the rod for three consecutive trials of 60 s duration each. Mice remaining on the rod for 60 s will received a perfect score. For each mouse, the average of five trials used as the score for final analysis.

Statistical Analysis

Student's unpaired t test was used to compare single means. One-way ANOVA was used to compare multiple means with Bonferonni's post-hoc analysis. Data were analyzed and graphed using GraphPad Prism software (v. 8.0.2; GraphPad Software). For all comparisons, statistical significance was set at p<0.05. Asterisks denote level of significance based on p value: *p<0.05, p<0.01, *p<0.001, and ****p<0.0001.

Example 2: CSTB Protein Expression and Extent of CSTB Distribution

Figure 2A:
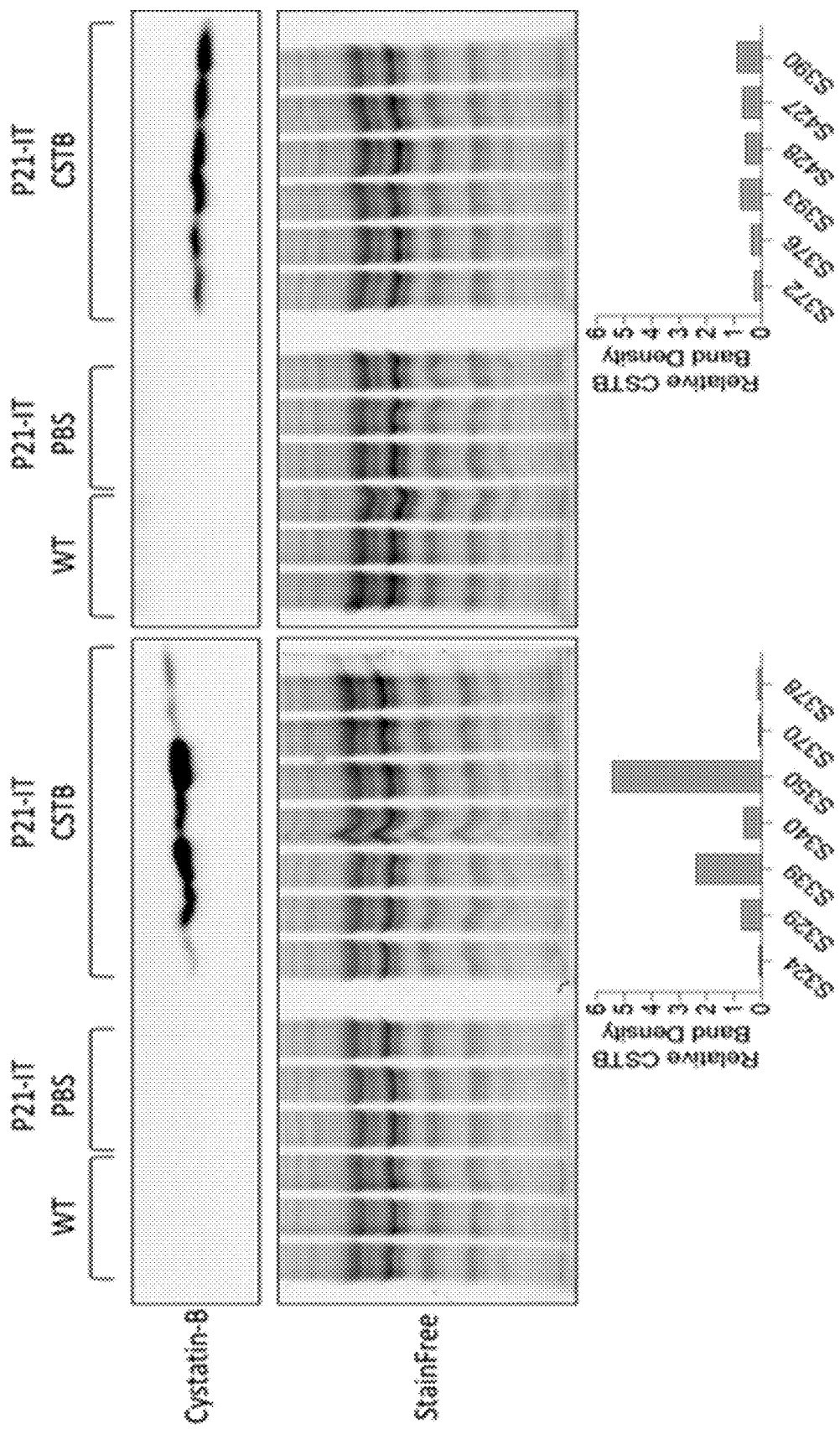
FIGS. 2A-2C show brain CSTB western blots with stain-free gel as loading control in Cstb$^{-/-}$ mouse model treated with AAV-CSTB.
Figure 2B:
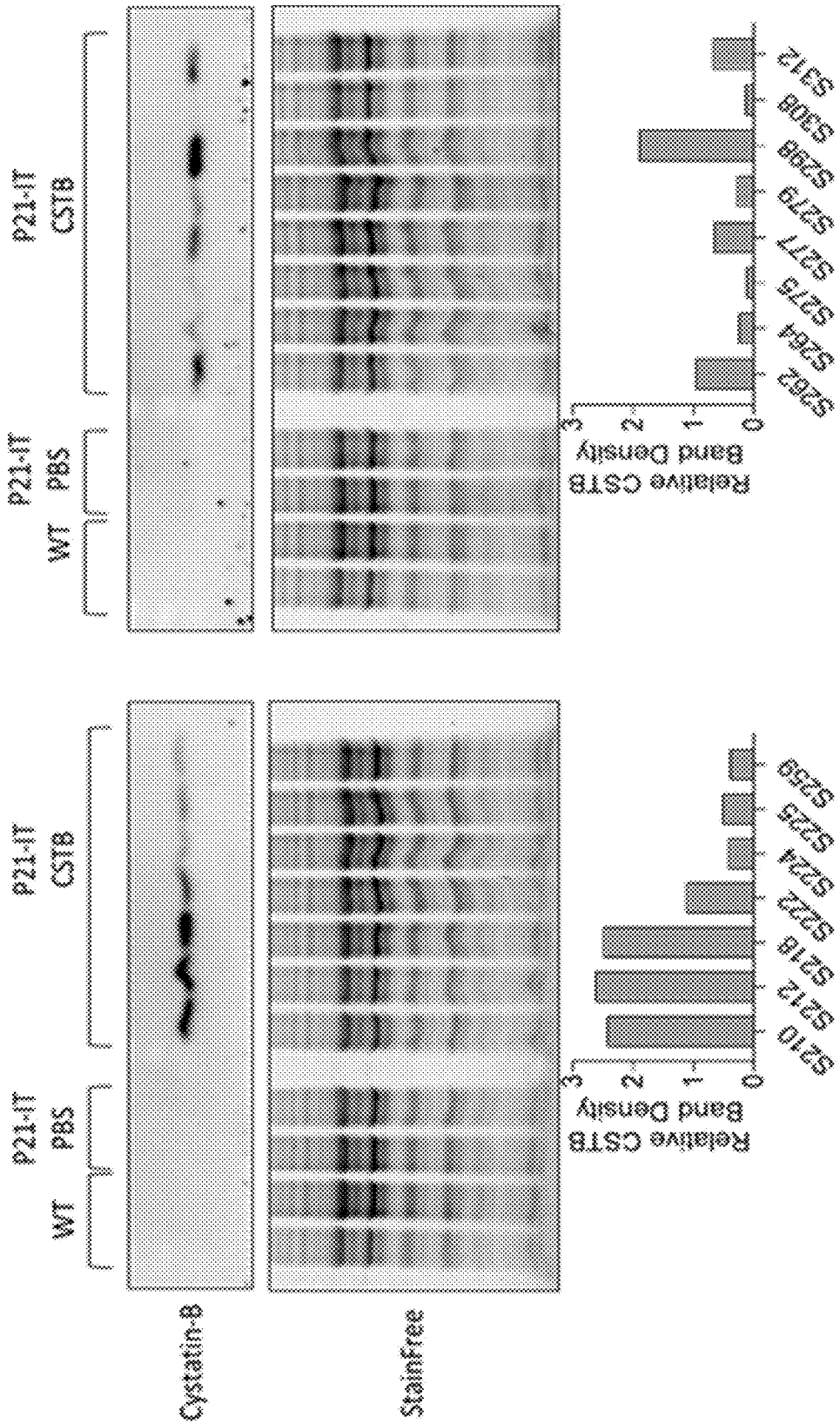
Figure 2C:
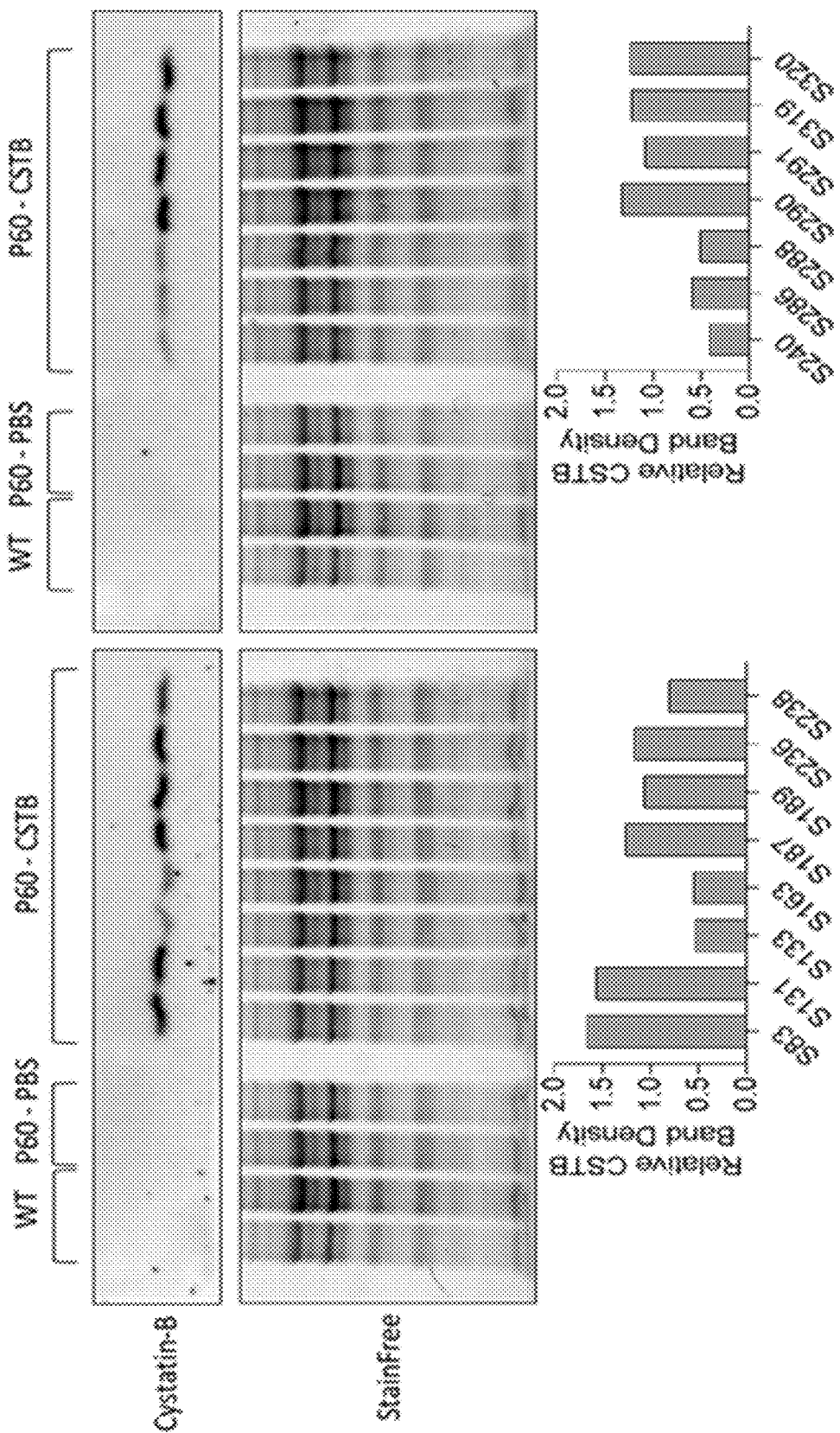

CSTB protein expression was measured by quantitative western blotting on whole hemisphere extract for all treated mice (FIGS. 2A-2C). The protein expression level was used to confirm the success of injections. The relative band intensity was normalized within the cohort.

Figure 3A:
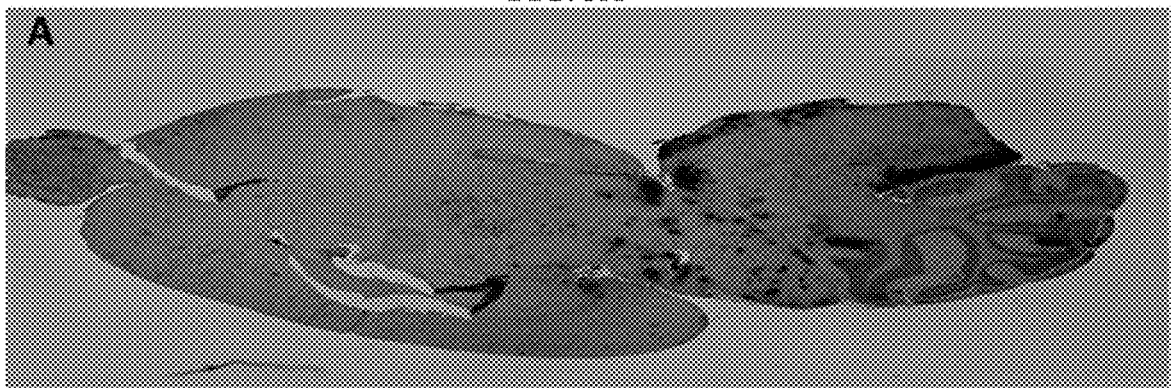
FIGS. 3A-3C show AAV-CSTB virus distribution as detected by CSTB immunohistochemistry.
Figure 3B:
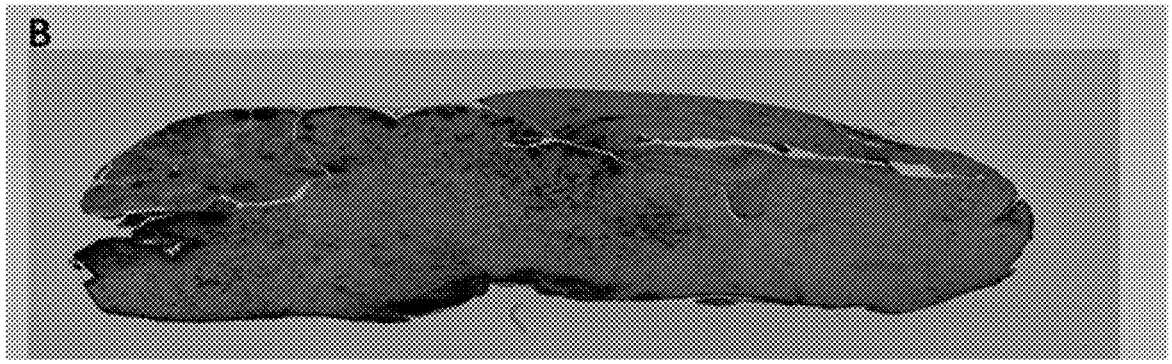
Figure 3C:
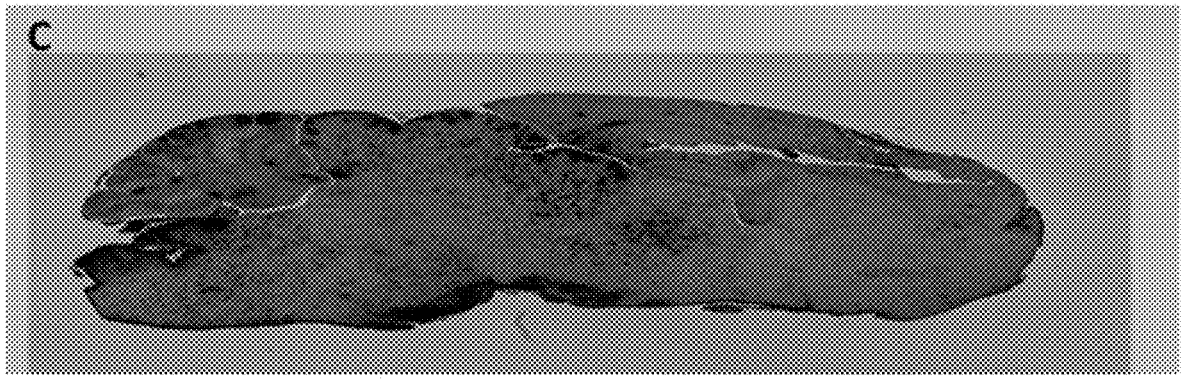
Figure 4A:
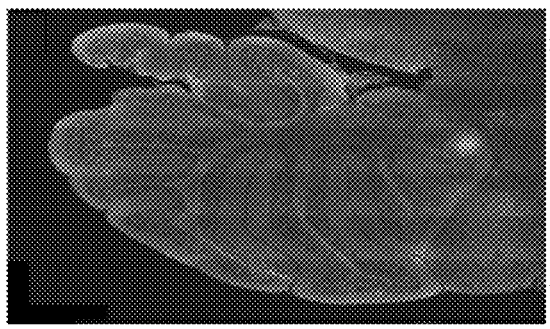
FIGS. 4A-4D show AAV-CSTB effect on granule cell apoptosis.
Figure 4B:
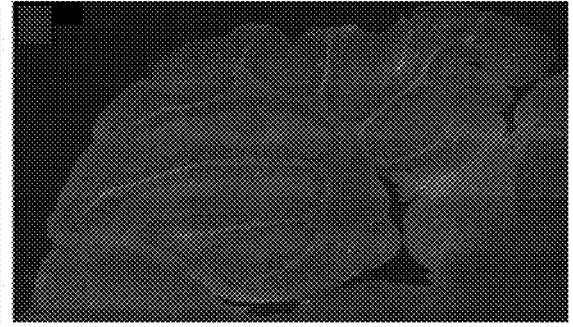
Figure 4C:
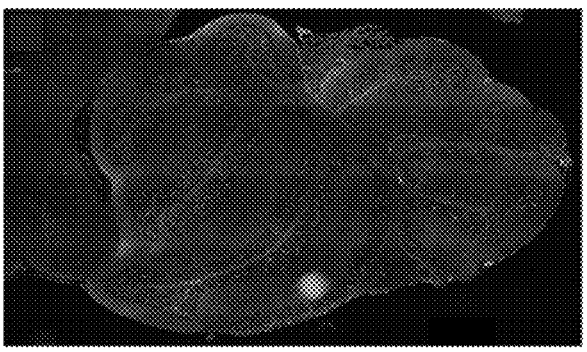
Figure 4D:
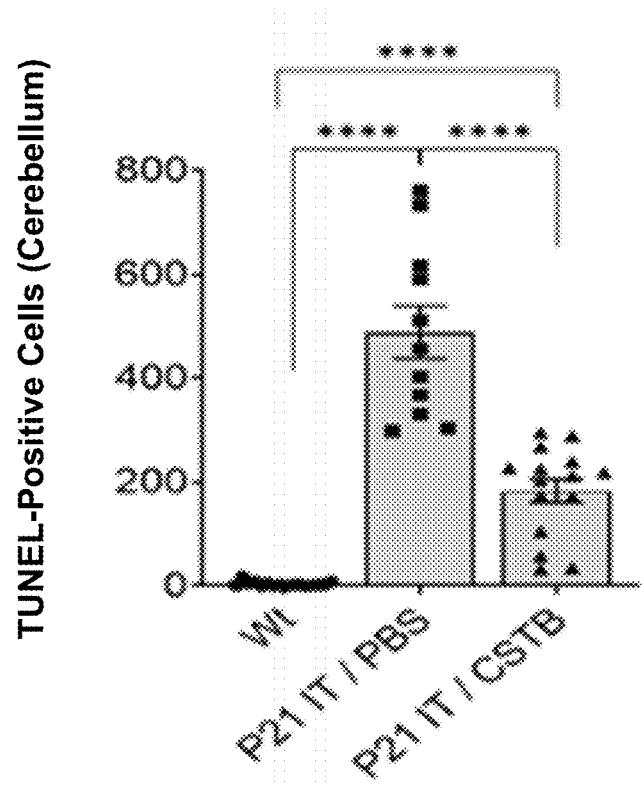
Figure 5C:
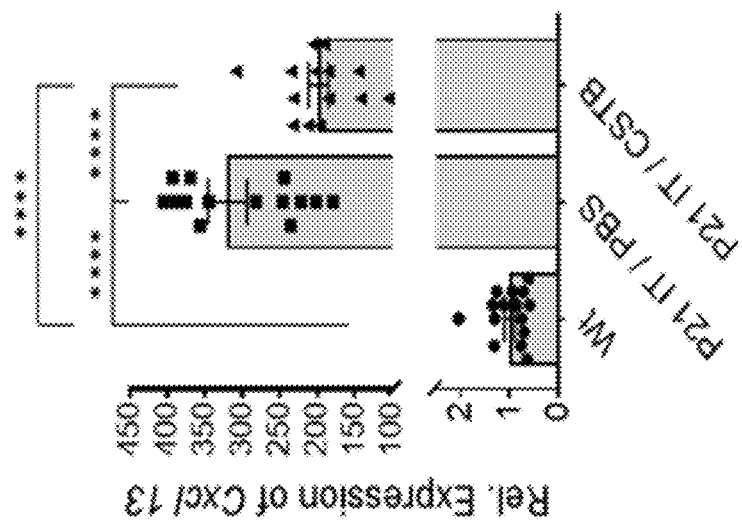
FIGS. 5A-5E show the effect of AAV-CSTB treatment on early-onset neuroinflammation as evaluated by relative mRNA expression levels analysis by qRT-PCR.
Figure 5B:
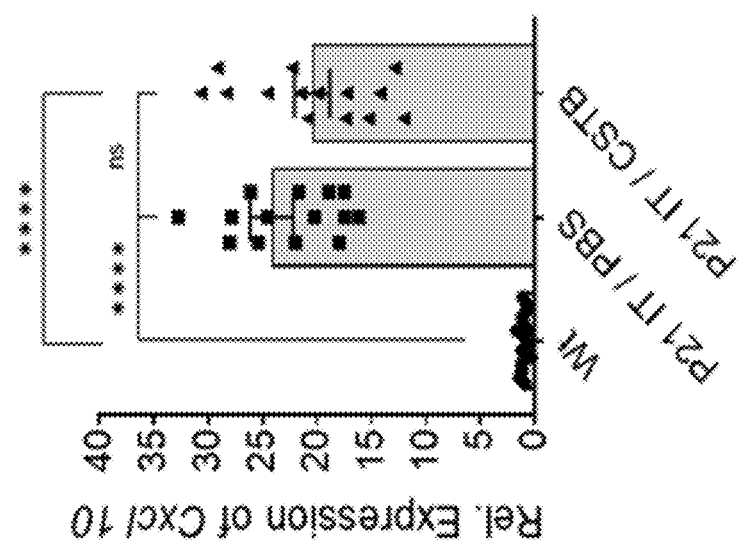
Figure 5A:
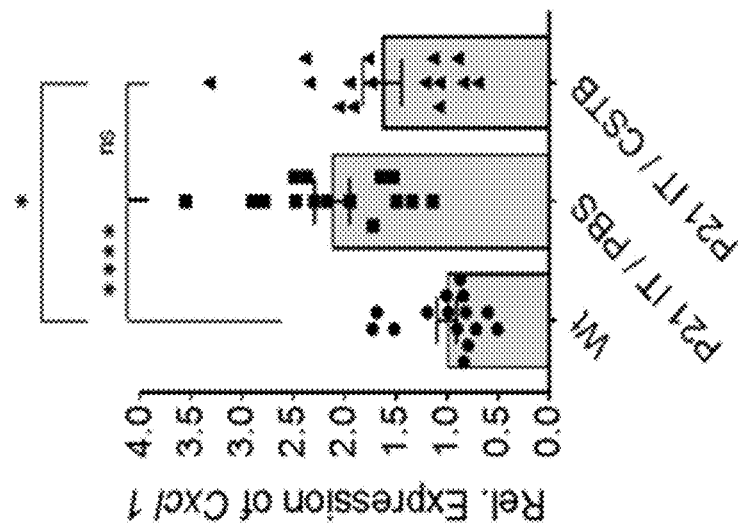
Figure 5E:
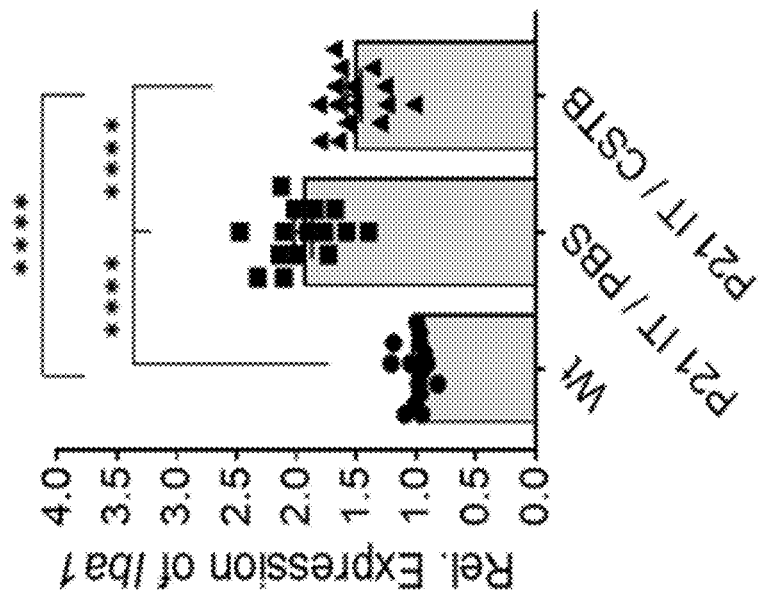
Figure 5D:
Figure 6A:
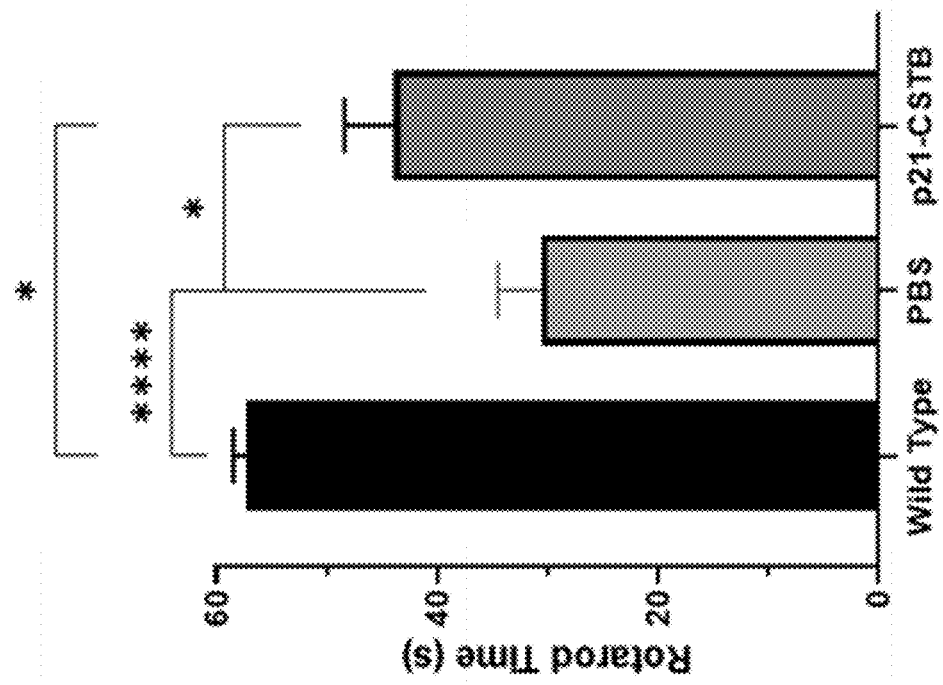
FIGS. 6A-6D show the effect of the treatment of Cstb$^{-/-}$ mice with AAV-CSTB on ataxia as measured by the analysis of motor coordination using stationary rod and accelerating (2 RPM) rod.
Figure 6B:
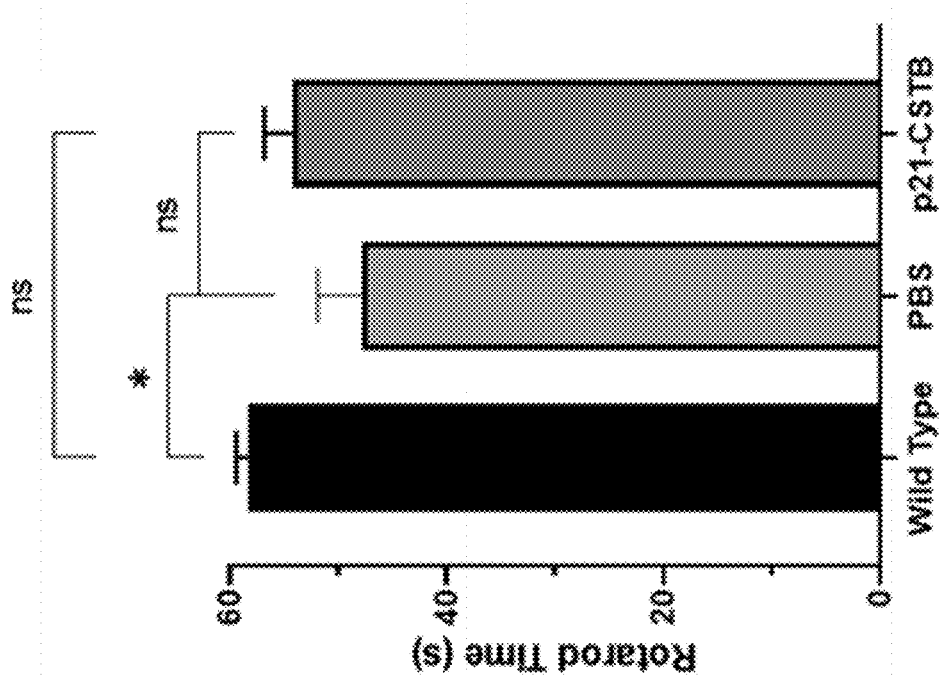
Figure 6D:
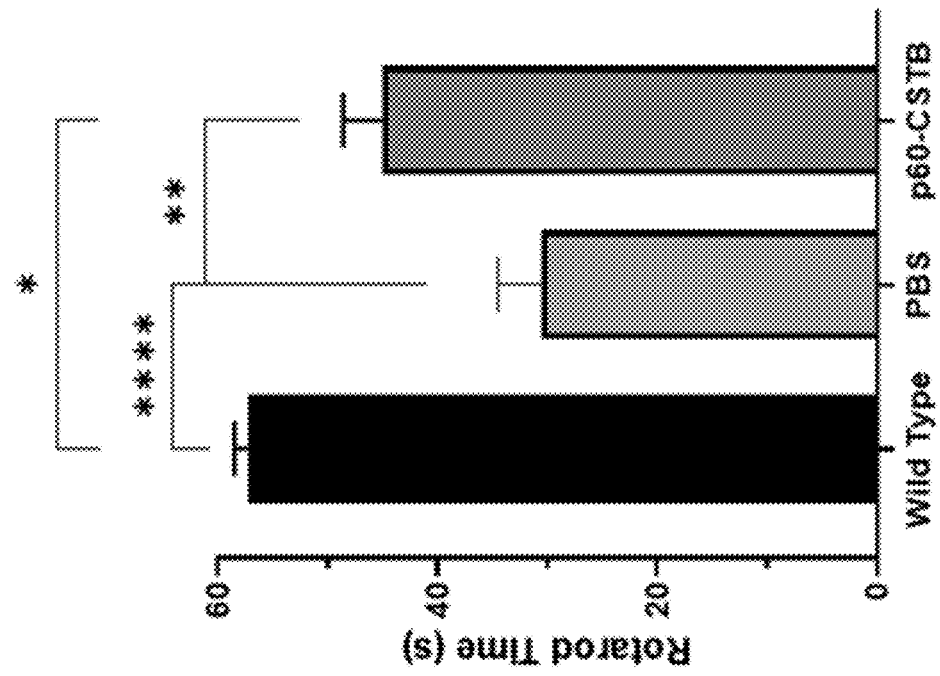
Figure 6C:
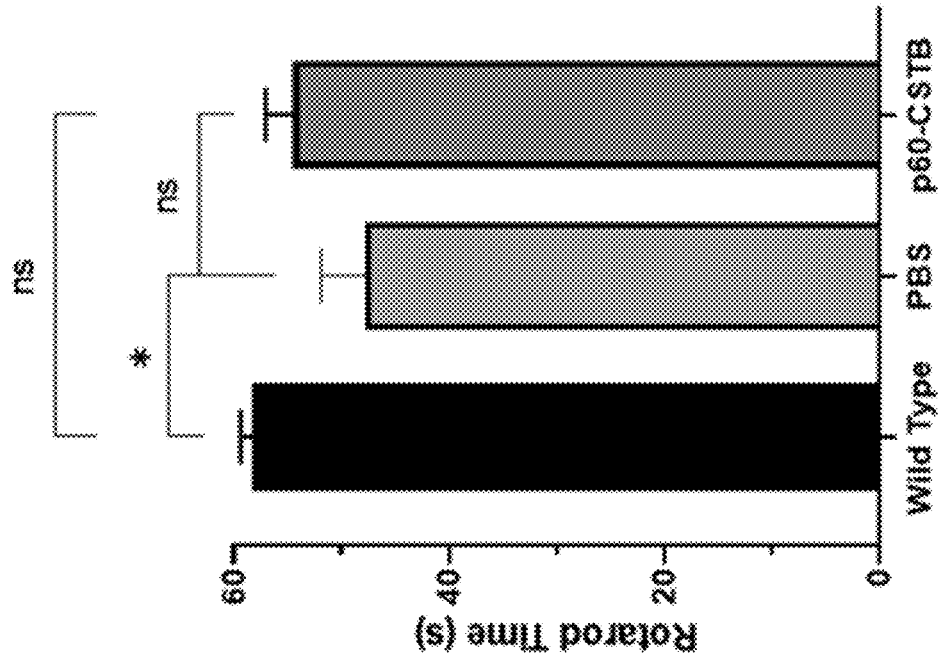
Figures 7A, 7B, 7C, 7D, 7E:
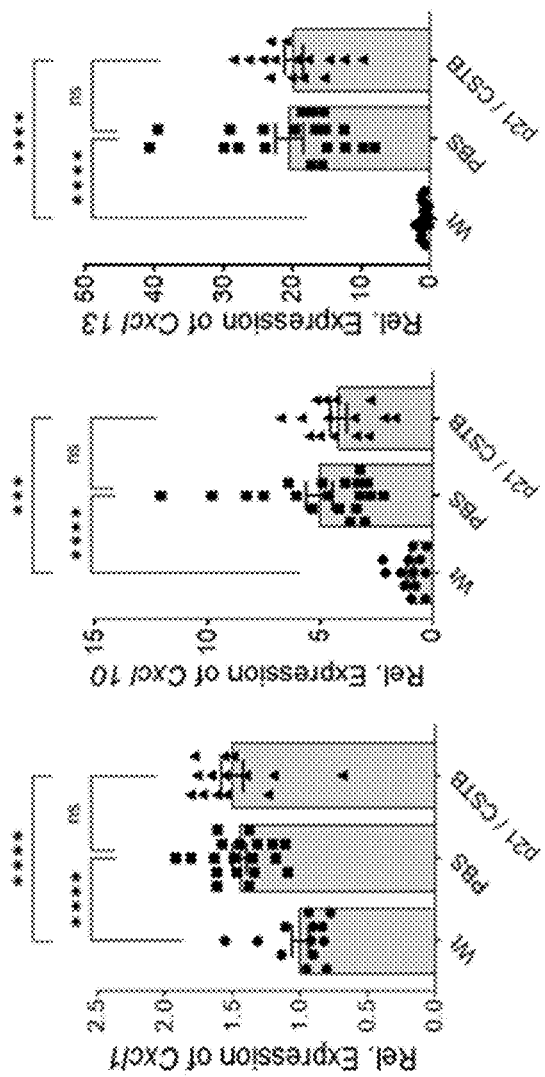
FIGS. 7A-7J show the effect of AAV-CSTB treatment on late-onset neuroinflammation as evaluated by relative mRNA expression levels analysis by qRT-PCR.
Figure 7F:
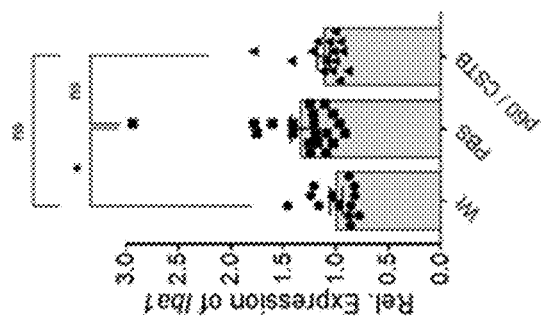
Figure 7G:
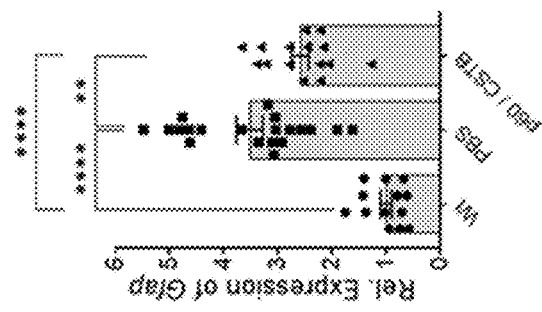
Figure 7H:
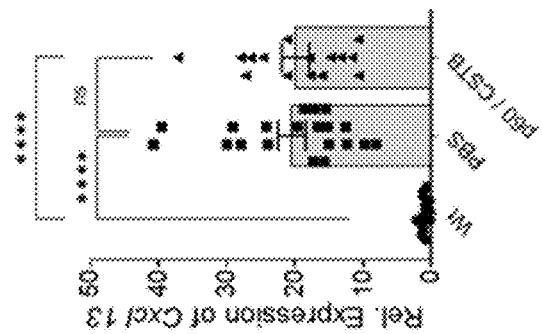
Figure 7I:
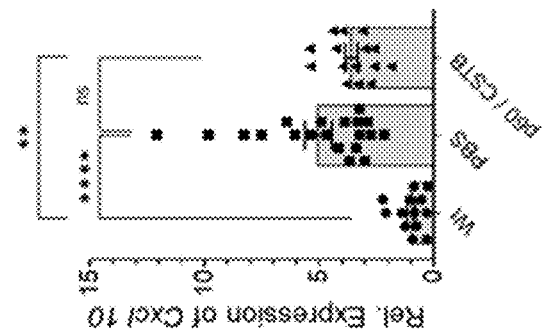
Figure 7J:
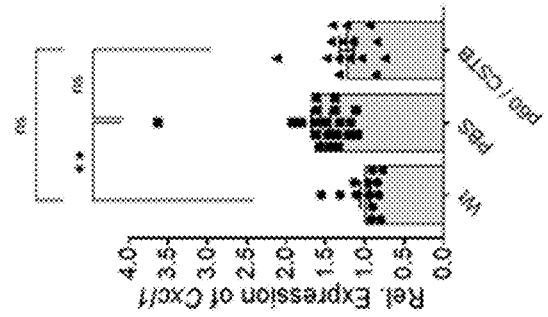

For a visual assessment of the pattern and extent of virally delivered CSTB distribution, immunohistochemistry using an anti-CSTB antibody was performed. Large numbers of cells expressed CSTB in cerebellum, brain stem and brain regions close to hindbrain. The level of expression was lower in the cortex, hippocampus and thalamic regions. The degree of CSTB-IHC stain was different in between the cohorts. Cohorts 2 and 3 show more densely stained (FIGS. 3A-3C).

Example 3: Effect of Gene Replacement Therapy on Granule Cell Apoptosis $Cstb^{-/-}$ mouse showed reduction in the density of the granule cell layer in the cerebellum compared with age-matched controls. Additionally, at higher magnifications granule cell layer exhibited numerous condensed (pyknotic) nuclei with a fragmented DNA characteristic of apoptosis. Although this apoptotic phenomenon observed in all ages, it was most prominent during early ages (~2 months). Granule cell apoptosis is one of the characteristic features of $Cstb^{-/-}$ mice. The number of apoptotic nuclei can be stained with TUNEL and quantified using image analysis tools. AAV-CSTB treated mice (Cohort-1) reduced the number of granule cell apoptosis up to 50% compared to PBS treated KO-Cstb$^{-/-}$ mice (FIGS. 4A-4D).

Example 4: Effect of Gene Replacement Therapy on Early-Onset Neuroinflammation One of the hallmarks of the Cstb mice is the early-onset neuroinflammation, which is detected as early as at P14 in restricted regions in the brain and becomes widespread as disease progresses. The expression of the five most studied immune marker genes that are upregulated at age of 2 months (Cxcl1, Cxcl10, Cxcl13, Gfap, and Iba1) was quantified. AAV-CSTB reduced the level of all immune markers in Cstb$^{-/-}$ mice (FIGS. 5A-5E).

Example 5: Effect of Gene Replacement Therapy on Ataxia

Starting from 6 months old, Cstb$^{-/-}$ mice show mild signs of ataxia when challenged to walk on uneven surfaces and significantly lose their ability to remain on both the still and rotating rod as they age. 7-9-month-old mice (N=~10-15) of each group from Cohorts 2 and 3 were tested for ataxia by using a rotarod test. Although, statistically there was no significant difference with stationary rod compared to PBS treated group, AAV-CSTB treated mice performed significantly better at 2-RPM rod (FIGS. 6A-6D).

Example 6: Effect of Gene Replacement Therapy on Late-Onset Neuroinflammation Although it is less severe, in older ages Cstb mice continue to show neuroinflammation and this phenomenon can be detected until the mice die. The same five immune marker genes that were used for early-onset neuroinflammation were used to see if they are still upregulated at later ages and tested whether the therapy can alleviate the ongoing neuroinflammation for the later stages of disease. It was found that, between the ages of 7-9 months, all of the tested markers (Cxcl1, Cxcl10, Cxcl13, Gfap, and Iba1) were upregulated albeit the expression levels were diminished compare to 2 months old age. AAV-CSTB therapy improved the level of few immune markers in Cstb$^{-/-}$ mice, but the overall reduction was not statistically significant compare to PBS (FIGS. 7A-7J).

Example 7: Effect of Gene Replacement Therapy on Brain Weight

Cstb$^{-/-}$ mice develop significant and progressive atrophy of the cerebral cortex and cerebellum from 2 months of age onward. This atrophy is due to severe neurodegeneration that follows the early-onset neuroinflammation and microglial activation. Cerebellar volume reduction reaches 50% by the age of 6 month without significant difference in the rate of volume loss between layers. The cortical volume loss coincides with the onset of cerebral atrophy at age of 2 months, and it is more prominent in some subcortical regions. In this study, the final brain-weight was used as an indirect measurement of neurodegeneration as described above. The total hemisphere weight was significantly higher in wild-type mice compare to AAV-CSTB or PBS treated mice in both 2 months of age (Cohort-1) and 7-9 months of age (Cohorts 2 and 3). AAV-CSTB treated mice did not prevent or reduce the brain loss compare to PBS treated mice (FIGS. 8A-8C).

Example 8: Conclusion

AAV-CSTB gene replacement therapy reduced early-onset neuroinflammation and decreases cerebellar granular cell death. AAV-CSTB gene therapy ameliorated behavioral phenotype (ataxia) and improves some of the late-onset neuroinflammation markers. AAV-CSTB gene therapy did not reduce or prevent the neurodegeneration related brain weight loss. In conclusion, replacing CSTB can provide therapeutic benefit in ULD mouse model (Cstb$^{-/-}$) by decreasing the severity of neuropathology.

Injections at early time-points (neonatal) and/or using different injection routes like intracerebroventricular injection (ICV) or intra-cisterna magna (ICM) can provide a greater benefit.

---

What is claimed is:

1. An expression cassette comprising:
   (a) SEQ ID NO:9;
   (b) SEQ ID NO:3, and SEQ ID NO:9; or
   (c) SEQ ID NO:2, SEQ ID NO:3, SEQ ID NO:9, SEQ ID NO:10, SEQ ID NO:11, SEQ ID NO:13, and SEQ ID NO:14.

2. The expression cassette of claim 1, wherein the expression cassette comprises SEQ ID NO:9, one or more promoters comprising SEQ ID NO:3, and one or more terminal repeats comprising SEQ ID NO:2, SEQ ID NO:11, or both.

3. The expression cassette of claim 1 further comprising SEQ ID NO:1.

4. A vector or vectors comprising the expression cassette of claim 1.

5. A recombinant adeno-associated virus (rAAV) vector comprising in 5' to 3' direction:
   (a) a first AAV inverted terminal repeat (ITR) sequence;
   (b) a promoter sequence;
   (c) a transgene nucleic acid molecule encoding for a CSTB polypeptide;
   (d) a polyA sequence; and
   (e) a second AAV ITR sequence,
wherein the transgene nucleic acid molecule encoding for a CSTB polypeptide comprises the nucleic acid sequence set forth in SEQ ID NO:9.

6. The rAAV vector of claim 5, wherein the first AAV ITR sequence comprises the nucleic acid sequence set forth in SEQ ID NO:2.

7. The rAAV vector of claim 5, wherein the second AAV ITR sequence comprises the nucleic acid sequence set forth in SEQ ID NO:11.

8. The rAAV vector of claim 5, wherein the promoter sequence comprises a Rous sarcoma virus (RSV) LTR promoter (optionally with the RSV enhancer), a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a CAG promoter, a hybrid chicken beta-actin promoter, an MeCP2 promoter, an EF1 promoter, a ubiquitous chicken β-actin hybrid (CBh) promoter, a U1a promoter, a U1b promoter, an MeCP2 promoter, an MeP418 promoter, an MeP426 promoter, a minimal MeCP2 promoter, a VMD2 promoter, an mRho promoter, an EFla promoter, an Ubc promoter, a human β-actin promoter, a TRE promoter, an Ac5 promoter, a Polyhedrin promoter, a CaMKIIa promoter, a Gall promoter, a TEF1 promoter, a GDS promoter, an ADH1 promoter, an Ubi promoter, or an α-1-antitrypsin (hAAT) promoter.

9. The rAAV vector of claim 5, wherein the promoter sequence comprises the nucleic acid sequence set forth in SEQ ID NO:3 or SEQ ID NO:5.

10. The rAAV vector of claim 5, wherein the polyA sequence comprises the nucleic acid molecule set forth in SEQ ID NO:10.

11. A recombinant adeno-associated virus (rAAV) vector comprising in 5' to 3' direction:
    (a) a first AAV ITR sequence comprising the nucleic acid sequence set forth in SEQ ID NO:2;
    (b) a promoter sequence comprising the nucleic acid sequence set forth in SEQ ID NO:3;
    (c) a transgene nucleic acid molecule as set forth in SEQ ID NO:9;
    (d) a polyA sequence comprising the nucleic acid sequence set forth in SEQ ID NO:10; and
    (e) a second AAV ITR sequence comprising the nucleic acid sequence set forth in SEQ ID NO:11.

12. The rAAV vector of claim 11, wherein the rAAV vector comprises the nucleic acid molecule set forth in SEQ ID NO:1.

13. A pharmaceutical composition comprising:
    the rAAV viral vector of claim 11, and at least one pharmaceutically acceptable excipient and/or additive.

* * * * *